US011667599B2

(12) United States Patent
Iwasaki et al.

(10) Patent No.: US 11,667,599 B2
(45) Date of Patent: Jun. 6, 2023

(54) METAL SALT OF AN ALICYCLIC DICARBOXYLIC ACID HAVING EXCELLENT DISPERSIBILITY IN POLYOLEFIN RESIN, PRODUCTION METHOD FOR SAID METAL SALT OF AN ALICYCLIC DICARBOXYLIC ACID, CRYSTAL NUCLEATING AGENT FOR POLYOLEFIN RESIN CONTAINING SAID METAL SALT OF AN ALICYCLIC DICARBOXYLIC ACID, CRYSTAL NUCLEATING AGENT COMPOSITION CONTAINING SAID CRYSTAL NUCLEATING AGENT, POLYOLEFIN RESIN COMPOSITION, AND POLYOLEFIN RESIN MOLDED ARTICLE

(71) Applicant: NEW JAPAN CHEMICAL CO., LTD., Kyoto (JP)

(72) Inventors: Shohei Iwasaki, Kyoto (JP); Kazuya Matsumoto, Kyoto (JP); Mitsuko Inoue, Kyoto (JP); Yurie Shinoda, Kyoto (JP); Sachio Kitagawa, Kyoto (JP); Yohei Uchiyama, Kyoto (JP)

(73) Assignee: NEW JAPAN CHEMICAL CO., LTD., Kyoto (JP)

( * ) Notice: Subject to any disclaimer, the term of this patent is extended or adjusted under 35 U.S.C. 154(b) by 78 days.

(21) Appl. No.: 17/275,282

(22) PCT Filed: Sep. 3, 2019

(86) PCT No.: PCT/JP2019/034513
§ 371 (c)(1),
(2) Date: Mar. 11, 2021

(87) PCT Pub. No.: WO2020/054492
PCT Pub. Date: Mar. 19, 2020

(65) Prior Publication Data
US 2022/0048846 A1 Feb. 17, 2022

(30) Foreign Application Priority Data
Sep. 11, 2018 (JP) .............................. JP2018-169457

(51) Int. Cl.
*C07C 61/09* (2006.01)
*C08K 5/098* (2006.01)
*C08K 5/00* (2006.01)
*C07C 51/083* (2006.01)
*C07C 51/36* (2006.01)
*C07C 51/41* (2006.01)
*C08L 23/00* (2006.01)

(52) U.S. Cl.
CPC ............ *C07C 61/09* (2013.01); *C07C 51/083* (2013.01); *C07C 51/36* (2013.01); *C07C 51/41* (2013.01); *C07C 51/412* (2013.01); *C08K 5/0083* (2013.01); *C08K 5/098* (2013.01); *C08L 23/00* (2013.01); *C07C 2601/14* (2017.05)

(58) Field of Classification Search
None
See application file for complete search history.

(56) References Cited

U.S. PATENT DOCUMENTS

| 3,207,737 A | 9/1965 | Wales |
| 3,207,739 A | 9/1965 | Wales |
| 7,332,536 B2 * | 2/2008 | Dotson ................. C07C 51/412 524/394 |
| 2009/0156744 A1 | 6/2009 | Ishii et al. |
| 2011/0105657 A1 | 5/2011 | Tanji et al. |
| 2019/0248980 A1 | 8/2019 | Iwasaki et al. |

FOREIGN PATENT DOCUMENTS

| CN | 106478985 A | 3/2017 |
| JP | H03252418 A | 11/1991 |
| JP | H07173342 A | 7/1995 |

(Continued)

OTHER PUBLICATIONS

Registry Number (RN) 2245698-12-6 in the STN registry, first available on Oct. 19, 2018. (Year: 2018).*
H. N. Beck et al; "Heterogeneous Nucleating Agents for Polypropylene Crystallization" Journal of Applied Polymer Science, vol. 11, (1967) pp. 673-685 (13 pages).
F. L. Binsbergen; "Heterogeneous nucleation in the crystallization of polyolefins: Part 1. Chemical and physical nature of nucleating agents" Shell Research N.V., pp. 253-267 (15 pages), 1970.
International Search Report issued in International Application No. PCT/JP2019/034513, dated Dec. 3, 2019 (2 pages).

(Continued)

*Primary Examiner* — Amy C Bonaparte
(74) *Attorney, Agent, or Firm* — Osha Bergman Watanabe & Burton LLP

(57) ABSTRACT

Provided is a metal salt of an alicyclic dicarboxylic acid with excellent dispersibility in polyolefin resins, and excellent crystallinity improving effect that is essential as a crystal nucleating agent for polyolefin resins, regardless of processing conditions. A method is also provided for producing the metal salt of an alicyclic dicarboxylic acid; a crystal nucleating agent containing the metal salt of an alicyclic dicarboxylic acid; a crystal nucleating agent composition for polyolefin resins containing the crystal nucleating agent and a fatty acid metal salt; a polyolefin resin composition containing the crystal nucleating agent; and a polyolefin resin molded article obtained using the polyolefin resin composition. Provided is a metal salt of an alicyclic dicarboxylic acid in which the alicyclic dicarboxylic acid is an alkyl substituent-containing cyclohexane-1,2-dicarboxylic acid, and the metal salt is a calcium salt, a hydroxyaluminum salt, a disodium salt, or a dilithium salt.

11 Claims, No Drawings

(56) References Cited

FOREIGN PATENT DOCUMENTS

| | | |
|---|---|---|
| JP | 2003313444 A | 11/2003 |
| JP | 2004524417 A | 8/2004 |
| JP | 2004525227 A | 8/2004 |
| JP | 2004531613 A | 10/2004 |
| JP | 2005120237 A | 5/2005 |
| JP | 2007509196 A | 4/2007 |
| JP | 2010084095 A | 4/2010 |
| JP | 2011042709 A | 3/2011 |
| JP | 2012097268 A | 5/2012 |
| JP | 2016501961 A | 1/2016 |
| JP | 2018044112 A | 3/2018 |
| WO | 2002078924 A2 | 10/2002 |
| WO | 2002079312 A1 | 10/2002 |
| WO | 02094759 A1 | 11/2002 |
| WO | 2005040259 A1 | 5/2005 |
| WO | 2007039997 A1 | 4/2007 |
| WO | 2007044122 A1 | 4/2007 |
| WO | 2008005143 A1 | 1/2008 |
| WO | 2014099144 A1 | 6/2014 |

OTHER PUBLICATIONS

Written Opinion issued in International Application No. PCT/JP2019/034513, dated Dec. 3, 2019 (5 pages).
Extended European Search Report issued in corresponding European Application No. 19859639.7; dated May 11, 2022 (9 pages).
Office Action issued in corresponding Japanese Application No. 2020-545931; dated Nov. 2, 2021 (8 pages).

* cited by examiner

METAL SALT OF AN ALICYCLIC DICARBOXYLIC ACID HAVING EXCELLENT DISPERSIBILITY IN POLYOLEFIN RESIN, PRODUCTION METHOD FOR SAID METAL SALT OF AN ALICYCLIC DICARBOXYLIC ACID, CRYSTAL NUCLEATING AGENT FOR POLYOLEFIN RESIN CONTAINING SAID METAL SALT OF AN ALICYCLIC DICARBOXYLIC ACID, CRYSTAL NUCLEATING AGENT COMPOSITION CONTAINING SAID CRYSTAL NUCLEATING AGENT, POLYOLEFIN RESIN COMPOSITION, AND POLYOLEFIN RESIN MOLDED ARTICLE

TECHNICAL FIELD

The present invention relates to a metal salt of an alicyclic dicarboxylic acid which has excellent dispersibility in polyolefin resins, and is thus excellent in crystallinity improving effect that is essential performance as a crystal nucleating agent for polyolefin resins, regardless of processing conditions. Specifically, the present invention relates to a metal salt of an alicyclic dicarboxylic acid with a specific structure which is capable of significantly improving the crystallization rate, i.e. the crystallization temperature, of a polyolefin resin when added to the polyolefin resin and which has excellent dispersibility in polyolefin resins; a crystal nucleating agent containing the metal salt; a polyolefin resin composition containing the crystal nucleating agent; and a polyolefin resin molded article obtained using the resin composition as a raw material.

BACKGROUND ART

Polyolefin resins such as polyethylene or polypropylene are inexpensive and have well-balanced properties, and therefore are used for various applications as general-purpose plastics. In general, in the case of crystalline resins, it is well known that improvement in crystallinity can improve, for example, molding processability thereof and the mechanical properties, thermal properties, and optical properties of the resulting molded articles. The same applies to polyolefin resins.

Methods for improving the crystallinity of a polyolefin resin by controlling the structure and composition of the resin have been extensively studied, and actually put into practical use. In particular, methods in which additives are added are widely used as simple and more practical methods. Crystal nucleating agents are typical additives capable of improving the crystallinity of resins. Various studies have been heretofore made on crystal nucleating agents, and crystal nucleating agents including inorganic compounds such as talc, organic compounds such as diacetal compounds, metal salts of phosphoric acid esters, and metal salts of carboxylic acids and sulfonic acids, and the like have been studied with various crystalline resins, and put into practical use.

Among the above-described crystal nucleating agents, metal salts of carboxylic acids have been long known to have an excellent nucleator effect. Typical examples thereof include sodium salts of benzoic acid and hydroxyaluminum salts of p-tert-butylbenzoic acid, which have been widely used for various applications (see Patent Literatures 1 and 2 and Non Patent Literatures 1 and 2).

Recently, metal salts of alicyclic carboxylic acids such as calcium salts and sodium salts of hexahydrophthalic acid and hydrogenated nadic acid have been reported to have an excellent effect as crystal nucleating agents for thermoplastic resins (Patent Literatures 3 to 7).

Normally, the metal salt-based crystal nucleating agents are not soluble in resin, and exhibit an effect as a crystal nucleating agent when dispersed in resin. Nucleation of resin is known to occur at a contact surface with the crystal nucleating agent. Accordingly, the effect of a dispersion type crystal nucleating agent such as a metal salt-based crystal nucleating agent exhibits a better effect as a nucleator as the contact area with resin increases, i.e. as the size of particles of the crystal nucleating agent decreases. However, since metal salt-based crystal nucleating agents have secondary aggregation properties, a decrease in particle size causes secondary aggregation. The resulting crystal nucleating agents have poor dispersibility in resin to be poorly dispersed depending on processing conditions, tending to fail to exhibit sufficient performance. Such a tendency has room for improvement.

Various studies have been heretofore made for the improvement. For example, in the case of the alicyclic carboxylic acids, methods of additionally using additives such as wax, fatty acid soap and silicon for improving dispersibility in resin and the like have been proposed (Patent Literatures 8 to 10). In the case of the metal salts of phosphoric acid esters, methods of additionally using additives such as fatty acid soap for improving dispersibility in resin and the like have been proposed (Patent Literatures 11 to 13).

However, additional use of different additives as described above cannot achieve an essential improvement, and therefore sufficient performance may not be achieved depending on processing conditions. Depending on the aimed application, some additives cannot be used together. In some cases, additives may lower the crystallinity improving effect which is an original purpose for adding a crystal nucleating agent. Improvement of these problems is desired.

In recent years, a changeover to plastics progresses in various applications with the aim of cost reduction, weight saving and the like. Among the plastics, polyolefin resins receive attention as most useful materials because they are inexpensive and lightweight. In the automotive field, reduction of fuel consumption is strongly required due to recent environmental issues and use of polyolefin resins most progresses. Recently, polyolefin resins have been used not only for small members but also for large members. In such fields, improvement of crystallinity by known crystal nucleating agents is not always sufficient, and further improvement of crystallinity is desired.

The above-described metal salt-based nucleators unfortunately have poor compatibility with different additives such as talc as a filler and calcium stearate as a neutralizer for remaining polymerization catalysts, and are often unable to exhibit sufficient performance when used in combination with such additives. This is a major hindrance to practical application.

Among the above-described automotive members, for example, members related to safety, such as bumpers, are required to be excellent in mechanical performance such as rigidity and strength. A polyolefin resin alone hardly provides sufficient mechanical performance to the resulting article, and is typically blended with a filler such as talc. In recent years, weight saving has been strongly required as described above, and it is a general trend that the amount of the filler is reduced as far as possible. However, reduction in amount of the filler unavoidably causes degradation of performance including mechanical performance. This has been a major issue to be addressed. As described above, crystal nucleating agents are capable of improving the crystallinity of polyolefin resins and the mechanical strength. An attempt has been therefore made to reduce or prevent the degradation of performance such as mechanical performance by addition of a crystal nucleating agent, and the crystal nucleating agent is actually used for this purpose. However, many of conventional crystal nucleating agents hardly exhibit a sufficient effect when used in combination with a filler, and it is currently difficult to meet the recently increasing demand for weight saving. Accordingly, development of a crystal nucleating agent which exhibits an excellent effect when used in combination with a filler such as talc is strongly desired.

CITATION LIST

Patent Literature

Patent Literature 1: U.S. Pat. No. 3,207,737
Patent Literature 2: U.S. Pat. No. 3,207,739
Patent Literature 3: JP 2004-525227 T
Patent Literature 4: JP 2004-524417 T
Patent Literature 5: JP 2004-531613 T
Patent Literature 6: JP 2007-509196 T
Patent Literature 7: JP 2012-97268 A
Patent Literature 8: JP 2016-501961 T
Patent Literature 9: WO 2007/044122
Patent Literature 10: WO 2008/005143
Patent Literature 11: JP 2003-313444 A
Patent Literature 12: JP 2005-120237 A
Patent Literature 13: WO 2007/039997

Non Patent Literature

Non Patent Literature 1: J. Appl. Poly. Sci., 11, pp. 673-685 (1967)
Non Patent Literature 2: Polymer, 11 (5), pp. 253-267 (1970)

SUMMARY OF INVENTION

Technical Problem

An object of the present invention is to provide a metal salt of an alicyclic dicarboxylic acid which has excellent dispersibility in polyolefin resins, and is thus excellent in crystallinity improving effect that is essential performance as a crystal nucleating agent for polyolefin resins, regardless of processing conditions; a method for producing the metal salt of an alicyclic dicarboxylic acid; a crystal nucleating agent for polyolefin resins containing the metal salt of an alicyclic dicarboxylic acid; a crystal nucleating agent composition for polyolefin resins containing the crystal nucleating agent and a fatty acid metal salt; a polyolefin resin composition containing the crystal nucleating agent; and a polyolefin resin molded article obtained using the polyolefin resin composition as a raw material.

Solution to Problem

In view of the situation in the art, the present inventors made extensive studies to solve the above problems. They found out that a metal salt of an alicyclic dicarboxylic acid with a specific structure has excellent dispersibility in polyolefin resin, and is thus excellent in crystallinity improving effect that is essential performance as a crystal nucleating agent for polyolefin resins, regardless of processing conditions, and that the effect can be further improved by further adding a fatty acid metal salt with a specific structure to the metal salt of an alicyclic dicarboxylic acid with a specific structure. The inventors thus completed the present invention.

The present invention provides, as described below, a metal salt of an alicyclic dicarboxylic acid which is a very excellent crystal nucleating agent for polyolefin resins; a production method thereof; a crystal nucleating agent and a crystal nucleating agent composition containing the metal salt of an alicyclic dicarboxylic acid; a polyolefin resin composition containing the crystal nucleating agent; and a polyolefin resin molded article obtained using the resin composition as a raw material.

The present invention provides a metal salt of an alicyclic dicarboxylic acid in which the alicyclic dicarboxylic acid is an alkyl substituent-containing cyclohexane-1,2-dicarboxylic acid and the metal salt is a calcium salt, a hydroxyaluminum salt, a disodium salt, or a dilithium salt.

In the metal salt of an alicyclic dicarboxylic acid of the present invention, the alkyl substituent is preferably a C1-C4 linear or branched alkyl group.

In the metal salt of an alicyclic dicarboxylic acid of the present invention, the alkyl substituent is preferably a methyl group or a tert-butyl group.

In the metal salt of an alicyclic dicarboxylic acid of the present invention, the alkyl substituent is preferably at the 3- or 4-position of the cyclohexane ring.

In the metal salt of an alicyclic dicarboxylic acid of the present invention, the metal salt is preferably a calcium salt or a disodium salt.

In the metal salt of an alicyclic dicarboxylic acid of the present invention, the molar ratio of a cis isomer in steric isomers of the alkyl substituent via a cyclohexane ring and an oxycarbonyl group forming the metal salt is preferably 70% or higher.

The method for producing the metal salt of an acyclic dicarboxylic acid of the present invention is a method for producing the metal salt of an alicyclic carboxylic acid, the method including step 1 of reacting a C5-C8 conjugated diene compound with maleic anhydride to prepare an alkyl substituent-containing 4-cyclohexene-1,2-dicarboxylic anhydride or a derivative thereof; step 2 of hydrogenating the alkyl substituent-containing 4-cyclohexane-1,2-dicarboxylic anhydride or a derivative thereof obtained in step 1 to prepare an alkyl substituent-containing cyclohexane-1,2-dicarboxylic anhydride or a derivative thereof; and step 3 of reacting the alkyl substituent-containing cyclohexane-1,2-dicarboxylic anhydride or a derivative thereof obtained in step 2 with a metal oxide, a metal hydroxide, or a metal chloride to prepare a metal salt of an alkyl substituent-containing cyclohexane-1,2-dicarboxylic acid.

The crystal nucleating agent of the present invention contains the metal salt of an alicyclic dicarboxylic acid of the present invention or a metal salt of an alicyclic dicarboxylic acid obtained by the method for producing the metal salt of an alicyclic dicarboxylic acid of the present invention.

The crystal nucleating agent composition for polyolefin resins of the present invention contains the crystal nucleating agent for polyolefin resins of the present invention, and a metal salt of a C12-C22 saturated or unsaturated fatty acid optionally having at least one hydroxy group in a molecule.

In the crystal nucleating agent composition for polyolefin resins of the present invention, a metal species of the metal salt of a C12-C22 saturated or unsaturated fatty acid optionally having at least one hydroxy group in a molecule is preferably lithium, magnesium, aluminum, or zinc.

The polyolefin resin composition of the present invention contains the crystal nucleating agent for polyolefin resins of the present invention, and a polyolefin resin.

The polyolefin resin composition of the present invention further contains a metal salt of a C12-C22 saturated or unsaturated fatty acid optionally having at least one hydroxy group in a molecule.

The polyolefin resin molded article of the present invention is obtained using the polyolefin resin composition of the present invention as a raw material.

Advantageous Effects of Invention

The metal salt of an alicyclic dicarboxylic acid of the present invention has very excellent dispersibility in polyolefin resins. Addition of the crystal nucleating agent of the present invention, i.e. a crystal nucleating agent containing the metal salt of an alicyclic dicarboxylic acid of the present invention, to a polyolefin resin can significantly improve the crystallization rate, i.e. the crystallization temperature, of the polyolefin resin. As a result, the molding cycle particularly for a large member or the like is considerably shortened, so that cost reduction, prevention of troubles during processing, and the like are very effectively achieved. Further, improvement in crystallinity of the polyolefin resin not only improves the mechanical performance (e.g., rigidity), optical performance (e.g., transparency), and thermal performance (e.g., heat resistance) of the resulting polyolefin resin molded article, but also reduces shrinkage and warpage, enabling stable production of a polyolefin resin molded article even in a complicated shape. Further, the crystal nucleating agent of the present invention can exhibit an excellent effect without suffering reduction in effect even when used in combination with a filler such as talc. The crystal nucleating agent composition for polyolefin resins of the present invention not only has very excellent dispersibility in polyolefin resins, but also can provide stable performance even when used in combination with different additives such as calcium stearate.

DESCRIPTION OF EMBODIMENTS

<Metal Salt of Alicyclic Dicarboxylic Acid>

The metal salt of an alicyclic dicarboxylic acid of the present invention is a metal salt of an alicyclic dicarboxylic acid with a specific structure and a specific metal species.

[Alicyclic Dicarboxylic Acid]

The alicyclic dicarboxylic acid according to the present invention is an alkyl substituent-containing cyclohexane-1,2-dicarboxylic acid. The alkyl substituent is preferably a C1-C4 linear or branched alkyl group, and specific examples thereof include a methyl group, an ethyl group, a n-propyl group, an isopropyl group, a n-butyl group, an isobutyl group, a sec-butyl group, and a tert-butyl group. Of these, a methyl group or a tert-butyl group is particularly recommendable from the viewpoint of a crystallization improving effect.

The alkyl substituent is preferably at the 3- or 4-position of the cyclohexane ring, and may be substituted at either position. The particularly preferred position of the alkyl substituent is appropriately selected according to the type of a metal species that forms a metal salt with the alkyl substituent.

The most prominent characteristic of the metal salt of an alicyclic dicarboxylic acid of the present invention is that the metal salt has excellent dispersibility in polyolefin resins, and thus exhibits a crystallinity improving effect which is essential performance as a crystal nucleating agent for polyolefin resins, regardless of processing conditions. The reason why the above-described characteristic can be obtained is that the alkyl substituent having a specific structure on the cyclohexane ring exhibits an effect of significantly improving dispersibility in polyolefin resins without impairing the performance as a crystal nucleating agent, i.e. a crystallinity improving effect. In general, a nonpolar alkyl substituent has an effect of improving compatibility with polyolefin resins which are also nonpolar polymers. If the compatibility becomes rather excessively high, an effect as a nucleator such as improvement of crystallinity tends to decrease. Effects of improving dispersibility in polyolefin resins and improving crystallinity can be both achieved only when substitution by an alkyl group with a specific structure is made in the metal salt of an alicyclic dicarboxylic acid of the present invention.

[Metal Salt]

The metal species of the metal salt of an alicyclic dicarboxylic acid of the present invention may be any metal species capable of exerting the effect of the present invention. Comprehensive evaluation from practical and performance points of view reveals that the metal species is preferably one selected from the group consisting of calcium, aluminum, sodium, and lithium. Among these, calcium or sodium is more preferable from the viewpoint of the crystallinity improving effect.

Specific examples of the metal salt of an alicyclic dicarboxylic acid of the present invention include disodium salts of 3-methylcyclohexane-1,2-dicarboxylic acid, calcium salts of 3-methylcyclohexane-1,2-dicarboxylic acid, hydroxyaluminum salts of 3-methylcyclohexane-1,2-dicarboxylic acid, dilithium salts of 3-methylcyclohexane-1,2-dicarboxylic acid, disodium salts of 3-ethylcyclohexane-1,2-dicarboxylic acid, calcium salts of 3-ethylcyclohexane-1,2-dicarboxylic acid, hydroxyaluminum salts of 3-ethylcyclohexane-1,2-dicarboxylic acid, dilithium salts of 3-ethylcyclohexane-1,2-dicarboxylic acid, disodium salts of 3-n-propylcyclohexane-1,2-dicarboxylic acid, calcium salts of 3-n-propylcyclohexane-1,2-dicarboxylic acid, hydroxyaluminum salts of 3-n-propylcyclohexane-1,2-dicarboxylic acid, dilithium salts of 3-n-propylcyclohexane-1,2-dicarboxylic acid, disodium salts of 3-isopropylcyclohexane-1,2-dicarboxylic acid, calcium salts of 3-isopropylcyclohexane-1,2-dicarboxylic acid, hydroxyaluminum salts of 3-isopropylcyclohexane-1,2-dicarboxylic acid, dilithium salts of 3-isopropylcyclohexane-1,2-dicarboxylic acid, disodium salts of 3-n-butylcyclohexane-1,2-dicarboxylic acid, calcium salts of 3-n-butylcyclohexane-1,2-dicarboxylic acid, hydroxyaluminum salts of 3-n-butylcyclohexane-1,2-dicarboxylic acid, dilithium salts of 3-n-butylcyclohexane-1,2-dicarboxylic acid, disodium salts of 3-tert-butylcyclohexane-1,2-dicarboxylic acid, calcium salts of 3-isobutylcyclohexane-1,2-dicarboxylic acid, hydroxyaluminum salts of 3-isobutylcyclohexane-1,2-dicarboxylic acid, dilithium salts of 3-isobutylcyclohexane-1,2-dicarboxylic acid, disodium salts of 4-methylcyclohexane-1,2-dicarboxylic acid, calcium salts of 4-methylcyclohexane-1,2-dicarboxylic acid, hydroxyaluminum salts of 4-methylcyclohexane-1,2-dicarboxylic acid, dilithium salts of 4-methylcyclohexane-1,2-dicarboxylic acid, disodium salts of 4-ethylcyclohexane-1,2-dicarboxylic acid, calcium salts of 4-ethylcyclohexane-1,2-dicarboxylic acid, hydroxyaluminum salts of 4-ethylcyclohexane-1,2-dicarboxylic acid, dilithium salts of 4-ethylcyclohexane-1,2-dicarboxylic acid, disodium salts of 4-n-propylcyclohexane-1,2-dicarboxylic acid, calcium salts of 4-n-propylcyclohexane-1,2-dicarboxylic acid, hydroxyaluminum salts of 4-n-propylcyclohexane-1,2-dicarboxylic acid, dilithium salts of 4-n-propylcyclohexane-1,2-dicarboxylic acid, disodium salts of 4-isopropylcyclohexane-1,2-dicarboxylic acid, calcium salts of 4-isopropylcyclohexane-1,2-dicarboxylic acid, hydroxyaluminum salts of 4-isopropylcyclohexane-1,2-dicarboxylic acid, dilithium salts of 4-isopropylcyclohexane-1,2-dicarboxylic acid, disodium salts of 4-n-butylcyclohexane-1,2-dicarboxylic acid, calcium salts of 4-n-butylcyclohexane-1,2-dicarboxylic acid, hydroxyaluminum salts of 4-n-butylcyclohexane-1,2-dicarboxylic acid, dilithium salts of 4-n-butylcyclohexane-1,2-dicarboxylic acid, disodium salts of 4-tert-butylcyclohexane-1,2-dicarboxylic acid, calcium salts of 4-tert-butylcyclohexane-1,2-dicarboxylic acid, hydroxyaluminum salts of 4-tert-butylcyclohexane-1,2-dicarboxylic acid, dilithium salts of 4-tert-butylcyclohexane-1,2-dicarboxylic acid, disodium salts of 4-isobutylcyclohexane-1,2-dicarboxylic acid, calcium salts of 4-isobutylcyclohexane-1,2-dicarboxylic acid, hydroxyaluminum salts of 4-isobutylcyclohexane-1,2-dicarboxylic acid, and dilithium salts of 4-isobutylcyclohexane-1,2-dicarboxylic acid. Preferred are disodium salts of 3-methylcyclohexane-1,2-dicarboxylic acid, calcium salts of 4-methylcyclohexane-1,2-dicarboxylic acid, and calcium salts of 4-tert-butylcyclohexane-1,2-dicarboxylic acid.

Of these, calcium salts or disodium salts are preferable as metal salts of an alicyclic dicarboxylic acid from the viewpoint of the crystallinity improving effect.

The metal salts of an alicyclic dicarboxylic acid of the present invention include two steric isomers: a cis isomer in which an alkyl substituent via the cyclohexane ring and an oxycarbonyl group forming a metal salt are directed in the same direction; and a trans isomer in which the alkyl substituent and the oxycarbonyl group are directed in different directions. As long as the effects of the present invention are exerted, the metal salt of an alicyclic dicarboxylic acid of the present invention does not depend on the structure of the isomer thereof, and may be any of a cis isomer, a trans isomer, or a mixture thereof. From the viewpoint of the crystallinity improving effect, it is desirable that the metal salt be rich in cis isomer. For example, the molar ratio of the cis isomer in the steric isomers is recommended to be 70% or higher, preferably 80% or higher, more preferably 90% or higher, still more preferably 95% or higher.

In the steric isomers of an alkyl substituent via the cyclohexane ring and an oxycarbonyl group forming the metal salt, the cis isomer means that an alkyl substituent on the cyclohexane ring and two oxycarbonyl groups forming the metal salt are all directed in the same direction.

In an exemplary method for measuring the molar ratio of the cis isomer, a steric isomer of an alicyclic dicarboxylic acid or a derivative thereof obtained in step 2 in the later-described method for producing the metal salt of an alicyclic dicarboxylic acid of the present invention is analyzed by gas chromatography (GC), the area ratios of the peaks are calculated by an area percentage method, and the molar ratio of the cis isomer is determined from the expression: [(area ratio of cis isomer)/(area ratio of cis isomer+area ratio of trans isomer)]×100.

The molar ratio of the cis isomer in the steric isomers does not change before and after the step of reacting an alicyclic dicarboxylic acid or a derivative thereof with a metal oxide, a metal hydroxide, or a metal chloride in step 3 in the later-described production method for the metal salt of an alicyclic dicarboxylic acid of the present invention.

By nuclear magnetic resonance spectroscopic analysis (NMR analysis) and infrared spectroscopic analysis (IR analysis), it can be determined that the compounds corresponding to the retention times in the gas chromatography (GC measurement) are identified to be the above-described alicyclic dicarboxylic acid or a derivative thereof and the cis isomer or the trans isomer thereof.

For example, in nuclear magnetic resonance spectroscopic analysis (NMR analysis) of 4-methylcyclohexane-1,2-dicarboxylic anhydride, an isomer structure can be determined from a nuclear overhauser effect (NOE) of methine hydrogen of an alkyl group-substituted part of the cyclohexane ring present near 1.4 ppm and methine hydrogen of a root part of an acid anhydride present near 3.2 ppm in the two-dimensional NMR spectrum obtained. It can be determined that the peak at which NOE is observed is attributed to the cis isomer, and the peak at which NOE is not observed is attributed to the trans isomer.

After the step of reacting an alicyclic dicarboxylic acid or a derivative thereof with a metal oxide, a metal hydroxide, or a metal chloride, infrared spectroscopic analysis (IR analysis) and induction coupled plasma analysis (ICP analysis) are performed to determine an element-specific spectrum, and the emission intensity thereof is measured to determine that an intended metal salt of an alicyclic dicarboxylic acid has been obtained.

The gas chromatography (GC measurement), nuclear magnetic resonance spectroscopic analysis (NMR analysis), infrared spectroscopic analysis (IR analysis), and induction coupled plasma analysis (ICP analysis) can be suitably performed under, for example, the conditions described in examples below.

The metal salts of an alicyclic carboxylic acid of the present invention include two steric isomers: a cis isomer in which two oxycarbonyl groups forming the metal salt are directed in the same direction; and a trans isomer in which the two oxycarbonyl groups are directed in different directions. In the present invention, as long as the effects of the present invention are exerted, the metal salt does not depend on the structure of the isomer thereof, and may be any of a cis isomer, a trans isomer, and a mixture thereof. From the viewpoint of the crystallinity improving effect, a cis isomer is preferred.

<Method for Producing Metal Salt of Alicyclic Dicarboxylic Acid>

The production method for an alicyclic dicarboxylic acid according to the present invention is not particularly limited as long as the effects of the present invention are exerted. The alicyclic dicarboxylic acid can be easily produced by method (a) in which an alkyl substituent-containing phthalic anhydride or a derivative thereof is hydrogenated to prepare an alkyl substituent-containing cyclohexane-1,2-dicarboxylic anhydride or a derivative thereof, and the obtained product is further formed into a metal salt; or method (b) in which an alkyl substituent-containing 4-cyclohexene-1,2-dicarboxylic anhydride or a derivative thereof obtained by the Diels-Alder method and the like is hydrogenated to prepare an alkyl substituent-containing cyclohexane-1,2-dicarboxylic anhydride or a derivative thereof, and the obtained product is further formed into a metal salt. As a preferred example, a specific example of method (b) will be described below in detail.

Step 1: A C5-C8 conjugated diene compound is reacted with maleic anhydride to prepare an alkyl substituent-containing 4-cyclohexene-1,2-dicarboxylic anhydride or a derivative thereof.

Step 2: The alkyl substituent-containing 4-cyclohexene-1,2-dicarboxylic anhydride or a derivative thereof obtained in step 1 is hydrogenated to prepare an alkyl substituent-containing cyclohexane-1,2-dicarboxylic anhydride or a derivative thereof.

Step 3: The alkyl-substituted cyclohexane-1,2-dicarboxylic anhydride or a derivative thereof obtained in step 2 is reacted with a metal oxide, a metal hydroxide, or a metal chloride to prepare a metal salt of alkyl substituent-containing cyclohexane-1,2-dicarboxylic acid of the present invention.

The method for producing the metal salt of an alicyclic dicarboxylic acid of the present invention includes steps 1 to 3 above.

That is, the present invention also encompasses a method for producing the metal salt of an alicyclic dicarboxylic acid including step 1 of reacting a C5-C8 conjugated diene compound with maleic anhydride to prepare an alkyl substituent-containing 4-cyclohexene-1,2-dicarboxylic anhydride or a derivative thereof; step 2 of hydrogenating the alkyl substituent-containing 4-cyclohexene-1,2-dicarboxylic anhydride or a derivative thereof obtained in step 1 to prepare an alkyl substituent-containing cyclohexane-1,2-dicarboxylic anhydride or a derivative thereof; and step 3 of reacting the alkyl substituent-containing cyclohexane-1,2-dicarboxylic anhydride or a derivative thereof obtained in step 2 with a metal oxide, a metal hydroxide, or a metal chloride to prepare a metal salt of an alkyl substituent-containing cyclohexane-1,2-dicarboxylic acid.

Examples of the C5-C8 conjugated diene compound include 2-methyl-1,3-butadiene (isoprene), 2-ethyl-1,3-butadiene, 2-butyl-1,3-butadiene, 2-tert-butyl-1,3-butadiene, 2,3-dimethyl-1,3-butadiene, 1,3-pentadiene (piperylene), 1,3-hexadiene, 2,4-hexadiene, 2,4-heptadiene and 2,4-octadiene.

Examples of the metal oxide, metal hydroxide, or metal chloride include oxides, hydroxides or, chlorides of a metal species such as calcium, aluminum, sodium, and lithium.

The method for step 1 of reacting a C5-C8 conjugated diene compound with maleic anhydride, the method for step 2 of hydrogenating an alkyl substituent-containing 4-cyclohexene-1,2-dicarboxylic anhydride or a derivative thereof and the method for step 3 of preparing a metal salt of an alkyl substituent-containing cyclohexane-1,2-dicarboxylic acid are not particularly limited, and known methods can be appropriately selected and used.

<Crystal Nucleating Agent for Polyolefin Resin>

The most prominent characteristic of the crystal nucleating agent for polyolefin resins of the present invention is that the crystal nucleating agent contains the metal salt of an alicyclic dicarboxylic acid of the present invention, or a metal salt of an alicyclic dicarboxylic acid obtained by the method for producing the metal salt of an alicyclic dicarboxylic acid of the present invention.

The crystal nucleating agent for polyolefin resins of the present invention may have any particle shape as long as the effects of the present invention are exerted. Considering that the crystal nucleating agent of the present invention is a dispersion-type crystal nucleating agent, reduction of the particle size to the extent that dispersibility in resin is not deteriorated due to secondary aggregation may increase the contact area with resin, enabling the crystal nucleating agent to exhibit more excellent performance in a smaller amount as described above. Accordingly, from the viewpoint of nucleator performance, the average of particle sizes determined by laser diffraction particle size distribution measurement is recommended to be 100 μm or less, preferably 50 μm or less, more preferably 20 μm or less, particularly preferably 10 μm or less. From the viewpoint of dispersibility, the average of particle sizes determined by laser diffraction particle size distribution measurement is recommended to be 0.01 μm or more, preferably 0.1 μm or more, still more preferably 0.5 μm or more.

<Crystal Nucleating Agent Composition for Polyolefin Resin>

The crystal nucleating agent for polyolefin resins of the present invention can be used in a crystal nucleating agent composition prepared as a formulation further containing a crystal nucleating agent other than the crystal nucleating agent of the present invention and various additives generally used for polyolefin resin within a range that the effect of the present invention is not impaired, if necessary.

In particular, a fatty acid metal salt is preferably used as it is expected to have an effect of further improving dispersibility in polyolefin resins.

The ratio of the crystal nucleating agent of the present invention to the fatty acid metal salt in the crystal nucleating agent composition (mass of crystal nucleating agent/mass of fatty acid metal salt) is recommended to be in the range of 5/1 to 1/4, preferably 4/1 to 1/3, more preferably 3/1 to 1/2, particularly preferably 2/1 to 1/1.

[Fatty Acid Metal Salt]

From the viewpoint of a dispersibility improving effect and the like, the fatty acid metal salt used for the crystal nucleating agent composition is recommended to be a metal salt of a C12-C22 saturated or unsaturated fatty acid optionally having at least one hydroxy group in the molecule.

The present invention also encompasses a crystal nucleating agent composition for polyolefin resins containing the crystal nucleating agent for polyolefin resins and a metal salt of a C12-C22 saturated or unsaturated fatty acid optionally having at least one hydroxy group in the molecule.

Specific examples of the fatty acid forming the metal salt of a C12-C22 saturated or unsaturated fatty acid optionally having at least one hydroxy group in the molecule include lauric acid, myristic acid, pentadecylic acid, palmitic acid, palmitoleic acid, margaric acid, stearic acid, oleic acid, vaccenic acid, linoleic acid, linolenic acid, 12-hydroxystearic acid, behenic acid, and erucic acid. Among these, lauric acid, myristic acid, palmitic acid, stearic acid, 12-hydroxystearic acid, or behenic acid is recommendable, and stearic acid or 12-hydroxystearic acid is most recommendable.

Specific examples of the metal species forming the metal salt of a C12-C22 saturated or unsaturated fatty acid optionally having at least one hydroxy group in the molecule include lithium, magnesium, barium, sodium, aluminum, potassium, strontium, and zinc. Among these, lithium, magnesium, aluminum, or zinc is recommendable, and lithium or zinc is most recommendable.

<Polyolefin Resin Composition>

The most prominent characteristic of the polyolefin resin composition of the present invention is that the polyolefin resin composition contains the crystal nucleating agent for polyolefin resins of the present invention and a polyolefin resin.

The polyolefin resin composition of the present invention can be easily obtained by dry-blending the polyolefin resin, the crystal nucleating agent for polyolefin resins, and optionally different additive(s) for polyolefin resins at room temperature and then melt-mixing the them under a predetermined condition.

The polyolefin resin composition can also be obtained by adding, if necessary, different additives for polyolefin resins to the crystal nucleating agent for polyolefin resins to prepare a crystal nucleating agent composition for polyolefin resins, dry-blending the composition and the polyolefin resin at room temperature, and then melting and mixing the resulting mixture under predetermined conditions.

The amount of the crystal nucleating agent for polyolefin resins in the polyolefin resin composition is not limited as long as an effect is exerted as a crystal nucleating agent. The amount is preferably 0.001 to 10 parts by mass, more preferably 0.01 to 5 parts by mass, per 100 parts by mass of the polyolefin resin.

[Polyolefin Resin]

The polyolefin resin is not limited as long as the effect of the present invention is exerted, and conventionally known polyolefin resins are usable. Examples of the polyolefin resin include polyethylene resins, polypropylene resins, polybutene resins, polymethylpentene resins, and polybutadiene resins. More specific examples thereof include high-density polyethylene, medium-density polyethylene, linear polyethylene, ethylene copolymers having an ethylene content of 50% by weight or higher, preferably 70% by weight or higher, propylene homopolymers, propylene copolymers having a propylene content of 50% by weight or higher, preferably 70% by weight or higher, butene homopolymers, butene copolymers having a butene content of 50% by weight or higher, preferably 70% by weight or higher, methylpentene homopolymers, methylpentene copolymers having a methylpentene content of 50% by weight or higher, preferably 70% by weight or higher, and polybutadiene. The above copolymers each may be a random copolymer or a block copolymer. Moreover, in the case where these resins are each a stereoregular resin, it may be an isotactic resin or a syndiotactic resin. Specific examples of comonomers that can constitute the copolymers include: C2-C12 α-olefins such as ethylene, propylene, butene, pentene, hexene, heptene, octene, nonene, decene, undecene, and dodecene; bicyclo monomers such as 1,4-endomethylenecyclohexene; (meth)acrylic acid esters such as methyl (meth)acrylate and ethyl (meth)acrylate; and vinyl acetate.

Examples of the catalyst usable for production of the polymer include, in addition to commonly used ziegler-natta catalysts, catalyst systems combining a catalyst including a carrier mainly containing a magnesium halide (e.g., magnesium chloride) and a transition metal compound (e.g., titanium halides such as titanium trichloride and titanium tetrachloride) supported on the carrier with an alkyl aluminum compound (e.g., triethyl aluminum, diethyl aluminum chloride), and metallocene catalysts.

The melt flow rate (hereafter, abbreviated as "MFR", JIS K 7210-1999) of the polyolefin resin according to the present invention is selected as appropriate according to the molding method employed. The MFR is recommended to be commonly about 0.01 to 200 g/10 min, preferably about 0.05 to 100 g/10 min.

[Different Additives]

As described above, the polyolefin resin composition of the present invention may contain different additive(s) for polyolefin resins according to the intended use or application thereof, within a range that the effect of the present invention is not impaired.

Examples of the additive for polyolefin resins include various additives listed in "The Tables of Positive Lists of Additives" edited by Japan Hygienic Olefin And Styrene Plastics Association (September, 2004). Specific examples of the various additives include fluorescent brighteners (e.g., 2,5-thiophene diyl(5-t-butyl-1,3-benzoxazole), 4,4'-bis(benzoxazol-2-yl)stilbene), antioxidants, stabilizers (e.g., metal compounds, epoxy compounds, nitrogen compounds, phosphorus compounds, sulfur compounds), ultraviolet absorbers (e.g., benzophenone compounds, benzotriazole compounds), surfactants, lubricants (e.g., aliphatic hydrocarbons such as paraffin and wax, C8-C22 higher fatty acids, C8-C22 higher fatty acid metal (such as Al, Ca) salts, C8-C22 higher aliphatic alcohols, polyglycol, esters of C4-C22 higher fatty acids and C4-C18 aliphatic monohydric alcohols, C8-C22 higher fatty acid amides, silicone oil, rosin derivatives), fillers (e.g., talc, hydrotalcite, mica, zeolite, perlite, diatom earth, calcium carbonate, glass fiber), foaming agents, foaming aids, polymer additives, plasticizers (e.g., dialkylphthalate, dialkylhexahydrophthalate), crosslinking agents, crosslinking accelerators, antistatic agents, flame retardants, dispersants, organic/inorganic pigments (e.g., indigo compounds, phthalocyanine compounds, anthraquinone compounds, ultramarine compounds, cobalt aluminate compounds), processing aids, neutralizers, and other nucleating agents.

Normally, a polyolefin resin composition containing a metal salt-based nucleator cannot exhibit sufficient performance when used in combination with calcium stearate and the like which is used as a lubricant or a neutralizer in many cases. The polyolefin resin composition of the present invention can exhibit sufficient performance even in the presence of calcium stearate and the like.

In the case where any of these additives is used, it may be used in a usual amount as long as the effect of the present invention is not disturbed. For example, the amount per 100 parts by mass of the polyolefin resin is normally preferably about 0.0001 to 100 parts by mass, more preferably about 0.001 to 50 parts by mass.

Examples of the antioxidant include phenolic antioxidants, phosphorous acid ester antioxidants, and sulfur antioxidants. Specific examples of the antioxidants include: phenolic antioxidants such as 2,6-di-tert-butylphenol, tetrakis[methylene-3-(3,5-tert-butyl-4-hydroxyphenyl)propionate]methane, and 2-hydroxy-4-methoxybenzophenone; sulfur antioxidants such as alkyl disulfide, thiodipropionic acid ester, and benzothiazole; and phosphorous acid ester antioxidants such as tris(nonylphenyl) phosphite, diphenyl isodecyl phosphite, triphenyl phosphite, tris(2,4-di-tert-butylphenyl)phosphite, and 3,9-bis(2,6-tert-butyl-4-methylphenoxy)-2,4,8,10-tetraoxa-3,9-diphosphaspiro[5,5]undecane. Among these, particularly recommended are tetrakis[methylene-3-(3,5-di-t-butyl-4-hydroxyphenyl)propionate] methane that is a phenolic antioxidant, and tris(2,4-di-tert-butylphenyl)phosphite and 3,9-bis(2,6-tert-butyl-4-methylphenoxy)-2,4,8,10-tetraoxa-3,9-diphosphaspiro[5,5] undecane that are phosphorous acid ester antioxidants.

From the viewpoint such as dispersibility of the crystal nucleating agent for polyolefin resins in polyolefin resins, and the like, it is particularly recommended that the polyolefin resin composition of the present invention contains a metal salt of a C12-C22 saturated or unsaturated fatty acid optionally having at least one hydroxy group in the molecule as a different additive.

Specific examples of the fatty acid forming the metal salt of a C12-C22 saturated or unsaturated fatty acid optionally having at least one hydroxy group in the molecule include lauric acid, myristic acid, pentadecylic acid, palmitic acid, palmitoleic acid, margaric acid, stearic acid, oleic acid, vaccenic acid, linoleic acid, linolenic acid, 12-hydroxystearic acid, behenic acid, and erucic acid. Among these, lauric acid, myristic acid, palmitic acid, stearic acid, 12-hydroxystearic acid, or behenic acid is recommended, and stearic acid or 12-hydroxystearic acid is most recommended.

Specific examples of the metal species of the metal salt of a C12-C22 saturated or unsaturated fatty acid optionally having at least one hydroxy group in the molecule include lithium, magnesium, barium, sodium, aluminum, potassium, strontium, and zinc. Among these, lithium, magnesium, aluminum, or zinc is recommended, and lithium or zinc is most recommended.

<Polyolefin Resin Molded Article>

The polyolefin resin molded article of the present invention is obtained using the polyolefin resin composition of the present invention as a raw material.

The polyolefin resin molded article of the present invention can be obtained by molding the polyolefin resin composition of the present invention in accordance with a conventional molding method. The molding method is not limited as long as the effects of the present invention are exerted. Any of known molding methods such as injection molding, extrusion molding, blow molding, pressure molding, rotational molding, and film molding can be employed.

In the case of the thus-obtained polyolefin resin molded article, the polyolefin resin has a high crystallization temperature. In other words, the crystallization rate is high. As a result, the molding cycle particularly for a large member or the like is considerably shortened, so that cost reduction, prevention of troubles during processing, and the like are very effectively achieved. Further, improvement of the crystallinity of the polyolefin resin not only improves the mechanical performance (e.g., rigidity), optical performance (e.g., transparency), and thermal performance (e.g., heat resistance) of the resulting polyolefin resin molded article, but also reduces shrinkage and warpage, enabling stable production of a polyolefin resin molded article even in a complicated shape. The polyolefin resin molded article is very useful for various applications such as automotive members, electric members, mechanical components and daily goods as molded articles, sheets, and films.

EXAMPLES

The present invention is more specifically described in the following with reference to, but not limited to, examples. The abbreviations of the compounds used in the examples, and the measurement process of each property are mentioned below.

[Analysis Method for Metal Salt of Alicyclic Dicarboxylic Acid Obtained]

(1) Gas Chromatography Analysis (GC Analysis)

The molar ratio of the cis isomer in the steric isomers of a 3- or 4-position alkyl substituent via a cyclohexane ring of an alicyclic dicarboxylic acid or a derivative thereof obtained in examples and an oxycarbonyl group forming a metal salt was measured by gas chromatography (GC). Thereafter, the area ratios of the peaks were calculated by an area percentage method, and the molar ratio of the cis isomer in the steric isomers of the 3- or 4-position alkyl substituent via the cyclohexane ring in the metal salt of an alicyclic dicarboxylic acid and the oxycarbonyl group forming the metal salt was determined from the expression: [(area ratio of cis isomer)/(area ratio of cis isomer+area ratio of trans isomer)]×100.

Comparison of the above molar ratio with the result of the similar measurement performed after converting the obtained metal salt of an alicyclic dicarboxylic acid back into an acid revealed that the molar ratio of the cis isomer in the steric isomers did not change before and after the step of reacting the alicyclic dicarboxylic acid or a derivative thereof with a metal oxide, a metal hydroxide, or a metal chloride.

The following nuclear magnetic resonance spectroscopic analysis (NMR analysis) and infrared spectroscopic analysis (IR analysis) revealed that the compounds corresponding to the respective retention times were the alicyclic dicarboxylic acid or a derivative thereof and the cis isomer or the trans isomer thereof.

<<GC Measurement Conditions>>

Type of equipment: Gas chromatograph GC-2010 (manufactured by Shimadzu Corporation)

Detector: FID, 280° C.

Column: DB-1701 (30 m×0.25 mmϕ×0.25 μm)

Column temperature: 145° C.

Injection temperature: 280° C.

Carrier gas: helium (line speed: 30 cm/sec)

Injection amount: 0.1 μl (sprit ratio: 1/15)

(2) Nuclear Magnetic Resonance Spectroscopic Analysis (NMR Analysis)

The structures of the isomers in the gas chromatography analysis (GC analysis) were determined by nuclear magnetic resonance spectroscopic analysis (NMR analysis). Measurement conditions for the NMR analysis are described below.

NMR analysis apparatus: trade name "DRX-500" manufactured by Bruker

Solvent: heavy dimethylsulfoxide (DMSO-d6)

Internal standard: tetramethylsilane (TMS)

Sample tube: 5 mm $^1$H-NMR . . . resonance frequency: 500.1 MHz, cumulative number: 4

$^{13}$C-NMR . . . resonance frequency: 125.8 MHz, cumulative number: 23

The measurement sample was prepared by diluting 30 mg of a sample with 0.8 ml of a solvent.

(3) Infrared Spectroscopic Analysis (IR Analysis)

The structures of the isomers in the gas chromatography analysis (GC analysis) and the structures of the metal salts of an alicyclic dicarboxylic acid obtained in the examples were determined by infrared spectroscopic analysis (IR analysis). Measurement conditions for the IR analysis are described below.

FT-IR apparatus: trade name "Spectrum One" manufactured by PerkinElmer

Measurement range: 650 to 4000 $cm^{-1}$

Measurement method: ATR method

Cumulative number: 3

Resolution: 4.00 $cm^{-1}$

The measurement was performed with the sample pressed onto the cell of the apparatus.

(4) Induction Coupled Plasma Analysis (ICP Analysis)

The structures of the metal salts of an alicyclic dicarboxylic acid obtained in the examples were determined by induction coupled plasma analysis (ICP analysis). Measurement conditions for the ICP analysis are described below.

ICP apparatus: trade name "iCAP 6500Duo" manufactured by Thermo Fisher SCIENTIFIC Spray chamber: cyclone sprayer Plasma conditions: plasma/aid/carrier=15/1.0/0.6

Plasma observation direction: three times in axial direction

The sample was pretreated by a microwave decomposition method to obtain a measurement sample.

Microwave apparatus: Multiwave PRO manufactured by Anton Paar

Decomposition conditions: about 0.05 g of the sample and 6 mL of nitric acid (special grade) were decomposed, and then diluted with distilled water to prepare the sample.

[Evaluation Method for Polyolefin Resin Composition]

(5) Crystallization Temperature

The crystallization temperature was measured in accordance with JIS K7121 (1987) using a differential scanning calorimetric analysis apparatus (DSC8500 manufactured by PerkinElmer). The evaluation sample used was about 6 mg of the polyolefin resin composition of each of the examples and comparative examples. The sample was set on the apparatus, held at 200° C. for three minutes, and then cooled at a cooling rate at 10° C./min. The top of the endothermic peak was defined as a crystallization temperature (° C.).

(6) Half-Crystallization Time ($T_{1/2}$)

The half-crystallization time was measured in accordance with JIS K7121 (1987) using a differential scanning calorimetric analysis apparatus (manufactured by PerkinElmer). The evaluation sample used was about 6 mg of the polyolefin resin composition of each of the examples and comparative examples. The sample was set on the apparatus, held at 200° C. for three minutes, then cooled to 140° C. at a cooling rate of 750° C./rain, and isothermally crystallized at this temperature. The time taken from the start of the isothermal crystallization until half the area of the exothermic peak based on the crystallization is reached in a relationship diagram between the time and the amount of heat was defined as a half-crystallization time ($T_{1/2}$ sec).

[Evaluation Method for Polyolefin Resin Molded Article]

(7) Cloudiness Degree (Haze Value)

The haze value (%) was measured by a method in conformity with JIS K7136 (2000) using a haze meter (NDH 7000) from Nippon Denshoku Industries Co., Ltd. The evaluation sample used was an olefin resin molded article in the form of a 0.5 mm-thick injection molded article. The smaller the value of the haze value obtained, the better the transparency.

(8) Flexural Modulus and Flexural Strength

The flexural modulus and the flexural strength were measured by a method in conformity with JIS K7171 (2016) using a universal material tester (manufactured by Instron). The test temperature was 25° C., and the test speed was 10 mm/min.

[Determination of Dispersibility in Polyolefin Resin Composition]

Polyolefin resin compositions containing a crystal nucleating agent blended with a polyolefin resin were prepared under three kneading conditions significantly different in kneading effect as described in the following examples, and the crystallization temperature and the half-crystallization time ($T_{1/2}$) of the obtained polyolefin resin composition were measured to determine the degree of the influence of the kneading effect.

The smaller the difference between the measurement results of the polyolefin resin compositions obtained under the three kneading conditions, the smaller the influence of the kneading effect. In general, the influence of the kneading effect tends to decrease as dispersibility in the polyolefin resin composition increases. The dispersibility in the polyolefin resin composition therefore is more excellent as the difference between values measured using the polyolefin resin compositions obtained under the following three kneading conditions is smaller.

Twin: using a twin-screw extruder and having a very high kneading effect.

Single50: using a single-screw extruder and having a moderate kneading effect when the rotation number is increased.

Single25: using a single-screw extruder and having a small kneading effect because the rotation speed is low.

Example 1

A pressure-resistant autoclave was charged with 196 g of maleic anhydride, 500 ppm of p-tert-butylcatechol as a radical polymerization inhibitor, and 500 ppm of diphenyl sulfide as a polymerization inhibition improver, and the mixture was melted under heating at 50° C. to 55° C. The inside of the system was then replaced under stirring with nitrogen gas containing 0.06 vol % oxygen. Thereafter, 140 g of isoprene (conjugated diene compound) was continuously added at 50° C. to 55° C. for six hours, and the mixture was subjected to Diels-Alder reaction at 70° C. for one hour. After completion of the reaction, the reaction product was distilled at 85° C. under normal pressure and then under reduced pressure to remove volatile components. Thus, 332 g of 4-methyl-4-cyclohexene-1,2-dicarboxylic anhydride was prepared.

Subsequently, a pressure-resistant autoclave was charged with 100 g of the 4-methyl-4-cyclohexene-1,2-dicarboxylic anhydride obtained above and 0.2 g of a palladium catalyst (palladium 5%/alumina 95%), and the mixture was subjected to hydrogenation reaction at a hydrogen pressure of 1 MPa and a temperature of 110° C. under stirring for five hours. After completion of the reaction, the reaction product was separated from the catalyst by a centrifugation method to prepare 197 g of 4-methylcyclohexane-1,2-dicarboxylic anhydride. Gas chromatography analysis and NMR analysis revealed that the molar ratio of the cis isomer of the obtained 4-methylcyclohexane-1,2-dicarboxylic anhydride was 85%.

For methine hydrogen of an alkyl group-substituted part of the cyclohexane ring present near 1.4 ppm and methine hydrogen of a root part of an acid anhydride present near 3.2 ppm in the two-dimensional NMR spectrum obtained, it was determined that the peak at which a nuclear overhauser effect (NOE) was observed was attributed to the cis isomer, and the peak at which NOE was not observed was attributed to the trans isomer.

Next, a four-neck flask equipped with a stirrer and a thermometer was charged with 500 ml of water and 61 g (0.81 mol) of calcium hydroxide, and the mixture was stirred at room temperature to form a slurry. To the obtained slurry was added 136 g (0.81 mol) of the 4-methylcyclohexane-1,2-dicarboxylic anhydride obtained above. The mixture was heated to 50° C., stirred for five hours, and reacted. After completion of the reaction, the slurry was separated by filtration. The residue was washed with a sufficient amount of water, and then dried overnight under reduced pressure at 140° C. to prepare 168 g of a 4-methylcyclohexane-1,2-dicarboxylic acid calcium salt (compound 1). IR analysis and ICP analysis revealed that the structure of the obtained compound 1 was a structure of an intended compound.

Example 2

The 4-methylcyclohexane-1,2-dicarboxylic anhydride obtained in Example 1 was distilled at 120° C. under reduced pressure to separate 20 g of a low-boiling-point fraction. Gas chromatography analysis and NMR analysis revealed that the molar ratio of the cis isomer in the obtained low-boiling-point fraction in the 4-methylcyclohexane-1,2-dicarboxylic anhydride was 99%.

Next, a four-neck flask equipped with a stirrer and a thermometer was charged with 50 ml of water and 6.1 g (0.08 mol) of calcium hydroxide, and the mixture was stirred at room temperature to form a slurry. To the obtained slurry was added 13.6 g (0.08 mol) of the 4-methylcyclohexane-1,2-dicarboxylic anhydride obtained above. The mixture was heated to 50° C., stirred for five hours, and reacted. After completion of the reaction, the slurry was separated by filtration. The residue was washed with a sufficient amount of water, and then dried overnight under reduced pressure at 140° C. to prepare 17.1 g of a 4-methylcyclohexane-1,2-dicarboxylic acid calcium salt (compound 2). IR analysis and ICP analysis revealed that the structure of the obtained compound 2 was a structure of an intended compound.

Example 3

The 4-methylcyclohexane-1,2-dicarboxylic anhydride (cis isomer molar ratio of 85%) obtained in Example 1 and the 4-methylcyclohexane-1,2-dicarboxylic anhydride (cis isomer molar ratio of 99%) obtained in Example 2 were blended at a ratio of 36/64 to prepare a 4-methylcyclohexane-1,2-dicarboxylic anhydride having a cis isomer molar ratio of 94%.

Next, a four-neck flask equipped with a stirrer and a thermometer was charged with 50 ml of water and 6.1 g (0.08 mol) of calcium hydroxide, and the mixture was stirred at room temperature to form a slurry. To the obtained slurry was added 13.6 g (0.08 mol) of the 4-methylcyclohexane-1,2-dicarboxylic anhydride obtained above. The mixture was heated to 50° C., stirred for five hours, and reacted. After completion of the reaction, the slurry was separated by filtration. The residue was washed with a sufficient amount of water, and then dried overnight under reduced pressure at 140° C. to prepare 15.9 g of a 4-methylcyclohexane-1,2-dicarboxylic acid calcium salt (compound 3). IR analysis and ICP analysis revealed that the structure of the obtained compound 3 was a structure of an intended compound.

Example 4

An amount of 330 g of 3-methyl-4-cyclohexene-1,2-dicarboxylic anhydride was prepared by carrying out Diels-Alder reaction and post-treatment as in Example 1 except that the conjugated diene compound used was trans-1,3-pentadiene instead of isoprene.

Subsequently, 200 g of the 3-methyl-4-cyclohexene-1,2-dicarboxylic anhydride obtained above was subjected to hydrogenation reaction and post-treatment as in Example 1 to prepare 198 g of 3-methylcyclohexane-1,2-dicarboxylic anhydride. Gas chromatography analysis and NMR analysis revealed that the molar ratio of the cis isomer of the obtained 3-methylcyclohexane-1,2-dicarboxylic anhydride was 88%.

For methine hydrogen of an alkyl group-substituted part of the cyclohexane ring present near 1.4 ppm and methine hydrogen of a root part of an acid anhydride present near 3.2 ppm in the two-dimensional NMR spectrum obtained, it was determined that the peak at which a nuclear overhauser effect (NOE) was observed was attributed to the cis isomer, and the peak at which NOE was not observed was attributed to the trans isomer.

Next, a four-neck flask equipped with a stirrer and a thermometer was charged with 65 g (0.39 mol) of 3-methylcyclohexane-1,2-dicarboxylic anhydride, 300 ml of water, and 32 g (0.8 mol) of sodium hydroxide, and the mixture was stirred at room temperature until the reaction system became homogeneous (heat was slightly generated during stirring). The obtained homogeneous solution was poured into acetone (6 L), and the precipitated white solid was separated by filtration, and the dried under reduced pressure at 110° C. to prepare 66 g of a 3-methylcyclohexane-1,2-dicarboxylic acid disodium salt (compound 4). IR analysis and ICP analysis revealed that the structure of the obtained compound 4 was a structure of an intended compound.

Example 5

A pressure-resistant autoclave was charged with 30 g of a 4-tert-butyl-phthalic acid dimethyl ester, 1.5 g of a rhodium catalyst (rhodium 5%/alumina 95%), and 120 g of methanol. The mixture was stirred at a hydrogen pressure of 3 MPa and 60° C. for four hours to be hydrogenated. After completion of the reaction, the reaction product was separated from the catalyst by a centrifugation method to prepare 31.7 g of a 4-tert-butylcyclohexane-1,2-dicarboxylic acid dimethyl ester.

Subsequently, a four-neck flask equipped with a stirrer and a thermometer was charged with 120 g of a 10% caustic soda aqueous solution and 50 ml of methanol, and 31.7 g of the 4-tert-butylcyclohexane-1,2-dicarboxylic acid dimethyl ester obtained above was dropwise added thereto. The mixture was then heated and stirred at 60° C. for three hours. After completion of the reaction, the reaction product was neutralized with 36.3 g of concentrated hydrochloric acid. The precipitated solid was separated by filtration, and the separated solid was then dried to prepare 23.8 g of 4-tert-butylcyclohexane-1,2-dicarboxylic acid. Gas chromatography analysis revealed that the molar ratio of the cis isomer of the obtained 4-tert-butylcyclohexane-1,2-dicarboxylic acid was 100%.

It was confirmed that only the cis isomer was obtained when 4-tert-butylcyclohexane-1,2-dicarboxylic acid was produced by the above-described method.

Next, a four-neck flask equipped with a stirrer and a thermometer was charged with 500 ml of water and 61 g (0.81 mol) of calcium hydroxide, and the mixture was stirred at room temperature to form a slurry. To the obtained slurry was added 34.5 g (0.15 mol) of 4-tert-butylcyclohexane-1,2-dicarboxylic acid obtained above. The mixture was heated to 50° C., and stirred for five hours to be reacted. After completion of the reaction, the slurry was separated by filtration. The residue was washed with a sufficient amount of water, and then dried overnight under reduced pressure at 140° C. to prepare 37 g of 4-tert-butylcyclohexane-1,2-dicarboxylic acid calcium salt (compound 5). IR analysis and ICP analysis revealed that the structure of the obtained compound 5 was a structure of an intended compound.

Example 6

A four-neck flask equipped with a stirrer and a thermometer was charged with 500 ml of water and 30.4 g (0.39 mol) of aluminum hydroxide, and the mixture was stirred at room temperature to form a slurry. To the obtained slurry was added 65 g (0.39 mol) of the 4-methylcyclohexane-1,2-dicarboxylic anhydride obtained in Example 3. The mixture was heated to 50° C., and stirred for five hours to be reacted. After completion of the reaction, the slurry was separated by filtration. The residue was washed with a sufficient amount of water, and then dried overnight under reduced pressure at 140° C. to prepare 60 g of a basic aluminum salt of 4-methylcyclohexane-1,2-dicarboxylic acid (compound 6).

IR analysis and ICP analysis revealed that the structure of the obtained compound 6 was a structure of an intended compound.

Example 7

A four-neck flask equipped with a stirrer and a thermometer was charged with 65 g (0.39 mol) of the 4-methylcyclohexane-1,2-dicarboxylic anhydride obtained in Example 3, 300 ml of water, and 19.2 g (0.8 mol) of lithium hydroxide. The mixture was stirred at room temperature until the reaction system became homogenous (heat was slightly generated during stirring). The obtained homogeneous solution was poured into acetone (6 L). The precipitated white solid was separated by filtration, and then dried under reduced pressure at 110° C. to prepare 60 g of a 4-methylcyclohexane-1,2-dicarboxylic acid dilithium salt (compound 7). IR analysis and ICP analysis revealed that the structure of the obtained compound 7 was a structure of an intended compound.

Example 8

An amount of 350 g of 4,5-dimethyl-4-cyclohexene-1,2-dicarboxylic anhydride was obtained by carrying out Diels-Alder reaction and post-treatment as in Example 1 except that the conjugated diene compound used was 169 g of 2,3-dimethylbutadiene instead of 140 g of isoprene.

Subsequently, 200 g of the 4,5-dimethyl-4-cyclohexene-1,2-dicarboxylic anhydride obtained above was subjected to hydrogenation reaction and post-treatment as in Example 1 to prepare 160 g of 4,5-dimethylcyclohexane-1,2-dicarboxylic anhydride.

Next, a four-neck flask equipped with a stirrer and a thermometer was charged with 65 g (0.39 mol) of the 4,5-dimethylcyclohexane-1,2-dicarboxylic anhydride obtained above, 300 ml of water, and 32 g (0.8 mol) of sodium hydroxide. The mixture was stirred at room temperature until the reaction system became homogeneous (heat was slightly generated during stirring). The obtained homogeneous solution was poured into acetone (6 L). The precipitated white solid was separated by filtration, and then dried under reduced pressure at 110° C. to prepare 66 g of a 4,5-dimethylcyclohexane-1,2-dicarboxylic acid disodium salt (compound 8). IR analysis and ICP analysis revealed that the structure of the obtained compound 8 was a structure of an intended compound.

Example 9

An amount of 320 g of 3,6-dimethyl-4-cyclohexene-1,2-dicarboxylic anhydride was prepared by carrying out Diels-Alder reaction and post-treatment as in Example 1 except that the conjugated diene compound used was 169 g of 2,4-hexadiene instead of 140 g of isoprene.

Subsequently, 200 g of the 3,6-dimethyl-4-cyclohexene-1,2-dicarboxylic anhydride obtained above was subjected to hydrogenation reaction and post-treatment as in Example 1 to prepare 170 g of 3,6-dimethylcyclohexane-1,2-dicarboxylic anhydride.

Next, a four-neck flask equipped with a stirrer and a thermometer was charged with 65 g (0.39 mol) of the 3,6-dimethylcyclohexane-1,2-dicarboxylic anhydride obtained above, 300 ml of water, and 19.2 g (0.8 mol) of lithium hydroxide. The mixture was stirred at room temperature until the reaction system became homogeneous (heat was slightly generated during stirring). The obtained homogeneous solution was poured into acetone (6 L). The precipitated white solid was separated by filtration, and then dried under reduced pressure at 110° C. to prepare 66 g of a 3,6-dimethylcyclohexane-1,2-dicarboxylic acid dilithium salt (compound 9). IR analysis and ICP analysis revealed that the structure of the obtained compound 9 was a structure of an intended compound.

Comparative Example 1

A four-neck flask equipped with a stirrer and a thermometer was charged with 30 g (0.18 mol) of the 4-methylcyclohexane-1,2-dicarboxylic anhydride obtained in Example 1, 150 ml of water, and 20.7 g (0.8 mol) of potassium hydroxide. The mixture was stirred at room temperature until the reaction system became homogeneous (heat was slightly generated during stirring). The obtained homogeneous solution was poured into acetone (3 L). The precipitated white solid was separated by filtration, and then dried under reduced pressure at 110° C. to prepare 33.9 g of a 4-methylcyclohexane-1,2-dicarboxylic acid dipotassium salt (compound 10). IR analysis and ICP analysis revealed that the structure of the obtained compound 10 was a structure of an intended compound.

Comparative Example 2

A four-neck flask equipped with a stirrer and a thermometer was charged with 50 ml of water and 6.1 g (0.08 mol) of calcium hydroxide, and the mixture was stirred at room temperature to form a slurry. To the obtained slurry was added 12.5 g (0.08 mol) of commercially available anhydrous cis-1,2-cyclohexanedicarboxylic acid (reagent manufactured by FUJIFILM Wako Pure Chemical Corporation). The mixture was heated to 50° C., stirred for five hours, and reacted. After completion of the reaction, the slurry was separated by filtration. The residue was washed with a sufficient amount of water, and then dried overnight under reduced pressure at 140° C. to prepare 15.8 g of a cyclohexane-1,2-dicarboxylic acid calcium salt (compound 11). IR analysis and ICP analysis revealed that the structure of the obtained compound 11 was a structure of an intended compound.

Example 10

An amount of 100 parts by mass of a polypropylene homopolymer (MFR: 30 g/10 min (load: 2160 g, temperature: 230° C.)) as a polyolefin resin, 0.1 parts by mass of the 4-methylcyclohexane-1,2-dicarboxylic acid calcium salt (compound 2) obtained in Example 2 as a crystal nucleating agent, and 0.05 parts by mass of tetrakis[methylene-3-(3,5-di-tert-butyl-4-hydroxyphenyl)propionate]methane (trade name "IRGANOX1010" manufactured by BASF Japan Ltd.) and 0.05 parts by mass of tris(2,4-di-tert-butylphenyl) phosphite (trade name "IRGAFOS168" manufactured by BASF Japan Ltd.) as different additives were dry-blended.

Next, three polyolefin resin compositions different in kneading effect were prepared in accordance with the following three conditions and methods using the dry-blended product obtained above. The crystallization temperatures and half-crystallization times of the three polyolefin resin compositions obtained were measured. Table 1 shows the results.

Twin: The dry-blended product is melted and mixed at a barrel temperature of 200° C. using a twin-screw extruder (manufactured by TECHNOVEL, L/D: 45, screw diameter:

15 mm, die diameter: 5 mm). The extruded strand is then cooled, and cut with a pelletizer to prepare a polyolefin resin composition.

Single50: The dry-blended product is melted and mixed at a barrel temperature of 200° C. using a single-screw extruder (manufactured by TECHNOVEL, L/D: 28, screw diameter: 25 mm, die diameter: 4 mm). The extruded strand is then cooled, and cut with a pelletizer to prepare a polyolefin resin composition.

Single25: The dry-blended product is melted and mixed at a barrel temperature of 200° C. using a single-screw extruder (manufactured by TECHNOVEL, L/D: 28, screw diameter: 25 mm, die diameter: 4 mm). The extruded strand is then cooled, and cut with a pelletizer to prepare a polyolefin resin composition.

Example 11

Three polyolefin resin compositions were prepared as in Example 10 except that the 4-tert-butylcyclohexane-1,2-dicarboxylic acid calcium salt (compound 5) obtained in Example 5 was used as a crystal nucleating agent. The crystallization temperatures and half-crystallization times of the three polyolefin resin compositions obtained were measured. Table 1 shows the results.

Comparative Example 3

Three polyolefin resin compositions were prepared as in Example 10 except that the cyclohexane-1,2-dicarboxylic acid calcium salt (compound 11) obtained in Comparative Example 2 was used as a crystal nucleating agent. The crystallization temperatures and half-crystallization times of the three polyolefin resin compositions obtained were measured. Table 1 shows the results.

TABLE 1

| | | Example | | Comparative Example |
|---|---|---|---|---|
| | | 10 | 11 | 3 |
| Crystal nucleator | | Compound 2 | Compound 5 | Compound 11 |
| Crystallization temperature (° C.) | twin | 136.0 | 135.9 | 132.4 |
| | single50 | 135.6 | 135.2 | 125.3 |
| | single25 | 135.2 | 135.1 | 122.5 |
| Half-crystallization time (seconds) | twin | 49 | 47 | 66 |
| | single50 | 55 | 53 | 108 |
| | single25 | 57 | 54 | 125 |

Example 12

An amount of 100 parts by mass of a polypropylene homopolymer (MFR: 30 g/10 min (load: 2160 g, temperature: 230° C.)) as a polyolefin resin, 0.2 parts by mass of the 4-methylcyclohexane-1,2-dicarboxylic acid calcium salt (compound 1) obtained in Example 1 as a crystal nucleating agent, and 0.05 parts by mass of tetrakis[methylene-3-(3,5-di-tert-butyl-4-hydroxyphenyl)propionate]methane (trade name "IRGANOX1010" manufactured by BASF Japan Ltd.) and 0.05 parts by mass of tris(2,4-di-tert-butylphenyl) phosphite (trade name "IRGAFOS168" manufactured by BASF Japan Ltd.) as different additives were dry-blended. The resulting dry-blended product was melted and mixed at a barrel temperature of 200° C. using a twin-screw extruder (manufactured by TECHNOVEL, L/D: 45, screw diameter: 15 mm, die diameter: 5 mm). The extruded strand was then cooled, and cut with a pelletizer to prepare a polyolefin resin composition. The crystallization temperature and the half-crystallization time of the polyolefin resin composition obtained were measured. Table 2 shows the results.

A polyolefin resin composition was prepared as in Example 12 except that the 4-methylcyclohexane-1,2-dicarboxylic acid dipotassium salt (compound 10) obtained in Comparative Example 1 was used instead of the compound 1. The crystallization temperature and half-crystallization time of the polyolefin resin composition obtained were measured. Table 3 shows the results.

Subsequently, the obtained polyolefin resin composition was molded under the conditions of an injection molding temperature (heating temperature) of 200° C. and a mold temperature (cooling temperature) of 40° C. with an injection molding machine (NS40-5A manufactured by Nissei Plastic Industrial Co., Ltd.) to prepare a polyolefin resin molded article (test piece) of the present invention. The flexural modulus and the haze value of the obtained test piece were measured. Table 2 shows the results.

Example 13

A polyolefin resin composition was prepared as in Example 12 except that the 4-methylcyclohexane-1,2-dicarboxylic acid calcium salt (compound 2) obtained in Example 2 was used instead of the compound 1. The crystallization temperature and half-crystallization time of the obtained polyolefin resin composition were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 14

A polyolefin resin composition was prepared as in Example 12 except that the 4-methylcyclohexane-1,2-dicarboxylic acid calcium salt (compound 3) obtained in Example 3 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and the haze value of the obtained test piece were measured. Table 2 shows the results.

Example 15

A polyolefin resin composition was prepared as in Example 12 except that the 3-methylcyclohexane-1,2-dicarboxylic acid disodium salt (compound 4) obtained in Example 4 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 16

A polyolefin resin composition was prepared as in Example 12 except that the 4-tert-butylcyclohexane-1,2- dicarboxylic acid calcium salt (compound 5) obtained in Example 5 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 17

A polyolefin resin composition was prepared as in Example 12 except that the basic aluminum salt of 3-methylcyclohexane-1,2-dicarboxylic acid (compound 6) obtained in Example 6 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 18

A polyolefin resin composition was prepared as in Example 12 except that the 4-methylcyclohexane-1,2-dicarboxylic acid dilithium salt (compound 7) obtained in Example 7 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 19

A polyolefin resin composition was prepared as in Example 12 except that the 4,5-dimethylcyclohexane-1,2-dicarboxylic acid disodium salt (compound 8) obtained in Example 8 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

Example 20

A polyolefin resin composition was prepared as in Example 12 except that the 3,6-dimethylcyclohexane-1,2-dicarboxylic acid dilithium salt (compound 9) obtained in Example 9 was used instead of the compound 1. The crystallization temperature and half-crystallization time of the polyolefin resin composition obtained were measured. Table 2 shows the results.

Subsequently, a polyolefin resin molded article (test piece) of the present invention was prepared as in Example 12 using the obtained polyolefin resin composition. The flexural modulus and haze value of the obtained test piece were measured. Table 2 shows the results.

TABLE 2

|  | Example | | | | | | | | |
| --- | --- | --- | --- | --- | --- | --- | --- | --- | --- |
|  | 12 | 13 | 14 | 15 | 16 | 17 | 18 | 19 | 20 |
| Crystal nucleator | Compound 1 | Compound 2 | Compound 3 | Compound 4 | Compound 5 | Compound 6 | Compound 7 | Compound 8 | Compound 9 |
| Crystallization temperature (° C.) | 134.7 | 136.4 | 135.4 | 134.6 | 136.4 | 130.3 | 132.4 | 133.5 | 133.3 |
| Half-crystallization time (seconds) | 55 | 36 | 46 | 53 | 41 | 101 | 73 | 68 | 75 |
| Haze value (%) | 21.6 | 21.5 | 21.5 | 17.6 | 17.8 | 9.4 | 18.6 | 13.0 | 15.2 |
| Fluxural modulus (MPa) | 1950 | 2020 | 1990 | 2060 | 1980 | 1830 | 1870 | 1930 | 1920 |

Comparative Example 4

A polyolefin resin composition was prepared as in Example 12 except that the 4-methylcyclohexane-1,2-dicarboxylic acid dipotassium salt (compound 10) obtained in Comparative Example 1 was used instead of the compound 1. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

Comparative Example 5

A polyolefin resin composition was prepared as in Example 12 except that the cyclohexane-1,2-dicarboxylic acid calcium salt (compound 11) obtained in Comparative Example 2 was used instead of the compound 1. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

Comparative Example 6

A polyolefin resin composition was prepared as in Example 12 except that a commercially available 2,2'-methylenebis-(4,6-di-tert-butylphenyl)phosphoric acid sodium salt (ADEKA STAB NA-11 manufactured by ADEKA CORPORATION; hereinafter abbreviated as NA-11) was used instead of the compound 1. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

Comparative Example 7

A polyolefin resin composition was prepared as in Example 12 except that a commercially available hydroxy-aluminum salt of p-tert-butylbenzoic acid (hereinafter, abbreviated as AL-PTBBA) was used instead of the compound 1. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

Comparative Example 8

A polyolefin resin composition was prepared as in Example 12 except that a commercially available sodium salt of benzoic acid (hereinafter, abbreviated as BA-Na) was used instead of the compound 1. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

Comparative Example 9

A polyolefin resin composition was prepared as in Example 12 without adding a crystal nucleating agent. The crystallization temperature and half-crystallization time of the polyolefin resin composition obtained were measured. Table 3 shows the results.

Subsequently, a polyolefin resin molded article (test piece) of the present invention was prepared as in Example 12 using the obtained polyolefin resin composition. The flexural modulus and haze value of the obtained test piece were measured. Table 3 shows the results.

TABLE 3

| | Comparative Example | | | | | |
|---|---|---|---|---|---|---|
| | 4 | 5 | 6 | 7 | 8 | 9 |
| Crystal nucleator | Compound 10 | Compound 11 | NA-11 | AL-PTBBA | BA-Na | — |
| Crystallization temperature (° C.) | 127.4 | 132.8 | 132.8 | 129.8 | 122.5 | 117.6 |
| Half-crystallization time (seconds) | 115 | 60 | 62 | 85 | 180 | >300 |
| Haze value (%) | 28.9 | 22.2 | 17.6 | 34.4 | 45.4 | 40.1 |
| Fluxural modulus (MPa) | 1800 | 1870 | 2110 | 1900 | 1650 | 1420 |

Example 21

A polyolefin resin composition was prepared as in Example 13 except that the amount of the compound 2 added was changed from 0.2 parts by mass to 0.05 parts by mass. The crystallization temperature and half-crystallization time of the polyolefin resin composition obtained were measured. Table 4 shows the results.

Subsequently, a polyolefin resin molded article (test piece) of the present invention was prepared as in Example 13 using the obtained polyolefin resin composition. The flexural modulus and haze value of the obtained test piece were measured. Table 4 shows the results.

Example 22

A polyolefin resin composition was prepared as in Example 21 except that the 4-tert-butylcyclohexane-1,2-dicarboxylic acid calcium salt (compound 5) obtained in Example 5 was used instead of the compound 2. The crystallization temperature and half-crystallization time of the polyolefin resin composition obtained were measured. Table 4 shows the results.

Subsequently, a polyolefin resin molded article (test piece) of the present invention was prepared as in Example 21 using the obtained polyolefin resin composition. The flexural modulus and haze value of the obtained test piece were measured. Table 4 shows the results.

Comparative Example 10

A polyolefin resin composition was prepared as in Example 21 except that the cyclohexane-1,2-dicarboxylic acid calcium salt (compound 11) obtained in Comparative Example 2 was used instead of the compound 2. The crystallization temperature and half-crystallization time of the polyolefin resin composition obtained were measured. Table 4 shows the results.

Subsequently, a polyolefin resin molded article (test piece) of the present invention was prepared as in Example 21 using the obtained polyolefin resin composition. The flexural modulus and haze value of the obtained test piece were measured. Table 4 shows the results.

Comparative Example 11

A polyolefin resin composition was prepared as in Example 21 except that commercially available NA-11 was used instead of the compound 2. The crystallization temperature and half-crystallization time of the polyolefin resin composition obtained were measured. Table 4 shows the results.

Subsequently, a polyolefin resin molded article (test piece) of the present invention was prepared as in Example 21 using the obtained polyolefin resin composition. The flexural modulus and haze value of the obtained test piece were measured. Table 4 shows the results.

TABLE 4

|  | Example | | Comparative Example | |
| --- | --- | --- | --- | --- |
|  | 21 | 22 | 10 | 11 |
| Crystal nucleator | Compound 2 | Compound 5 | Compound 11 | NA-11 |
| Crystallization temperature (° C.) | 135.9 | 135.6 | 132.1 | 130.9 |
| Half-crystallization time (seconds) | 45 | 47 | 64 | 71 |
| Haze value (%) | 21.9 | 18.2 | 22.9 | 18.9 |
| Fluxural modulus (MPa) | 1970 | 1880 | 1760 | 2050 |

Example 23

An amount of 100 parts by mass of linear low-density polyethylene (MFR: 20 g/10 min (load: 2160 g, temperature: 190° C.)) as a polyolefin resin, 0.2 parts by mass of the 3-methylcyclohexane-1,2-dicarboxylic acid disodium salt (compound 4) obtained in Example 4 as a crystal nucleating agent, and 0.05 parts by mass of tetrakis[methylene-3-(3,5-di-tert-butyl-4-hydroxyphenyl)propionate]methane (trade name "IRGANOX1010" manufactured by BASF Japan Ltd.) and 0.05 parts by mass of tris(2,4-di-tert-butylphenyl) phosphite (trade name "IRGAFOS168" manufactured by BASF Japan Ltd.) as different additives were dry-blended. The resulting dry-blended product was melted and mixed at a barrel temperature of 200° C. using a twin-screw extruder (manufactured by TECHNOVEL, L/D: 45, screw diameter: 15 mm, die diameter: 5 mm). The extruded strand was then cooled, and cut with a pelletizer to prepare a polyolefin resin composition. The crystallization temperature of the polyolefin resin composition obtained was measured. Table 5 shows the result.

Subsequently, the obtained polyolefin resin composition was molded under the conditions of an injection molding temperature (heating temperature) of 200° C. and a mold temperature (cooling temperature) of 40° C. with an injection molding machine (NS40-5A manufactured by NISSEI PLASTIC INDUSTRIAL CO., LTD.) to prepare a polyolefin resin molded article (test piece) of the present invention. The haze value of the obtained test piece was measured. Table 5 shows the result.

Example 24

A polyolefin resin composition was prepared as in Example 23 except that the 4-methylcyclohexane-1,2-dicarboxylic acid calcium salt (compound 1) obtained in Example 1 was used instead of the compound 4. The crystallization temperature of the polyolefin resin composition obtained was measured. Table 5 shows the result.

Subsequently, a polyolefin resin molded article (test piece) of the present invention was prepared as in Example 23 using the obtained polyolefin resin composition. The haze value of the obtained test piece was measured. Table 5 shows the result.

Example 25

A polyolefin resin composition was prepared as in Example 23 except that the 4-tert-butylcyclohexane-1,2-dicarboxylic acid calcium salt (compound 5) obtained in Example 5 was used instead of the compound 4. The crystallization temperature of the polyolefin resin composition obtained was measured. Table 5 shows the result.

Subsequently, a polyolefin resin molded article (test piece) of the present invention was prepared as in Example 23 using the obtained polyolefin resin composition. The haze value of the obtained test piece was measured. Table 5 shows the result.

Comparative Example 12

A polyolefin resin composition was prepared as in Example 23 except that the cyclohexane-1,2-dicarboxylic acid calcium salt (compound 11) obtained in Comparative Example 2 was used instead of the compound 4. The crystallization temperature of the polyolefin resin composition obtained was measured. Table 5 shows the result.

Subsequently, a polyolefin resin molded article (test piece) of the present invention was prepared as in Example 23 using the obtained polyolefin resin composition. The haze value of the obtained test piece was measured. Table 5 shows the result.

Comparative Example 13

A polyolefin resin composition was prepared as in Example 23 except that NA-11 was used instead of the compound 4. The crystallization temperature of the polyolefin resin composition obtained was measured. Table 5 shows the result.

Subsequently, a polyolefin resin molded article (test piece) of the present invention was prepared as in Example 23 using the obtained polyolefin resin composition. The haze value of the obtained test piece was measured. Table 5 shows the result.

Comparative Example 14

A polyolefin resin composition was prepared as in Example 23 without adding a crystal nucleating agent. The crystallization temperature of the polyolefin resin composition obtained was measured. Table 5 shows the result.

Subsequently, a polyolefin resin molded article (test piece) of the present invention was prepared as in Example 23 using the obtained polyolefin resin composition. The haze value of the obtained test piece was measured. Table 5 shows the result.

TABLE 5

| | Example | | | Comparative Example | | |
|---|---|---|---|---|---|---|
| | 23 | 24 | 25 | 12 | 13 | 14 |
| Crystal nucleator | Compound 4 | Compound 1 | Compound 5 | Compound 11 | NA-11 | — |
| Crystallization temperature (° C.) | 115.5 | 113.2 | 115.0 | 114.4 | 113.4 | 109.1 |
| Haze value (%) | 58.0 | 59.5 | 52.6 | 61.9 | 59.6 | 66.2 |

Example 26

An amount of 70 parts by mass of a polypropylene homopolymer (MFR: 30 g/10 min (load: 2160 g, temperature: 230° C.)) as a polyolefin resin, 30 parts by mass of a 70%-talc master batch (manufactured by Shiraishi Calcium Kaisha Ltd.) as a filler, 0.1 parts by mass of the 4-methylcyclohexane-1,2-dicarboxylic acid calcium salt (compound 2) obtained in Example 2 as a crystal nucleating agent, and 0.05 parts by mass of tetrakis[methylene-3-(3,5-di-tert-butyl-4-hydroxyphenyl)propionate]methane (trade name "IRGANOX1010" manufactured by BASF Japan Ltd.) and 0.05 parts by mass of tris(2,4-di-tert-butylphenyl)phosphite (trade name "IRGAFOS168" manufactured by BASF Japan Ltd.) as different additives were dry-blended. The resulting dry-blended product was melted and mixed at a barrel temperature of 200° C. using a twin-screw extruder (manufactured by TECHNOVEL, L/D: 45, screw diameter: 15 mm, die diameter: 5 mm). The extruded strand was then cooled, and cut with a pelletizer to prepare a polyolefin resin composition. The crystallization temperature of the polyolefin resin composition obtained was measured. Table 6 shows the result.

Subsequently, the obtained polyolefin resin composition was molded under the conditions of an injection molding temperature (heating temperature) of 200° C. and a mold temperature (cooling temperature) of 40° C. with an injection molding machine (NS40-5A manufactured by NISSEI PLASTIC INDUSTRIAL CO., LTD.) to prepare a polyolefin resin molded article (test piece) of the present invention. The flexural modulus and flexural strength of the obtained test piece were measured. Table 6 shows the results.

Comparative Example 15

A polyolefin resin composition was prepared as in Example 26 except that the cyclohexane-1,2-dicarboxylic acid calcium salt (compound 11) obtained in Comparative Example 2 was used instead of the compound 2. The crystallization temperature of the polyolefin resin composition obtained was measured. Table 6 shows the result.

Subsequently, a polyolefin resin molded article (test piece) was prepared as in Example 26 using the obtained polyolefin resin composition. The flexural modulus and flexural strength of the obtained test piece were measured. Table 6 shows the results.

Comparative Example 16

A polyolefin resin composition was prepared as in Example 26 except that NA-11 was used instead of the compound 2. The crystallization temperature of the polyolefin resin composition obtained was measured. Table 6 shows the result.

Subsequently, a polyolefin resin molded article (test piece) was prepared as in Example 26 using the obtained polyolefin resin composition. The flexural modulus and flexural strength of the obtained test piece were measured. Table 6 shows the results.

Comparative Example 17

A polyolefin resin composition was prepared as in Example 26 without adding a crystal nucleating agent. The crystallization temperature of the polyolefin resin composition obtained was measured. Table 6 shows the result.

Subsequently, a polyolefin resin molded article (test piece) was prepared as in Example 26 using the obtained polyolefin resin composition. The flexural modulus and flexural strength of the obtained test piece were measured. Table 6 shows the results.

TABLE 6

| | Example | Comparative Example | | |
|---|---|---|---|---|
| | 26 | 15 | 16 | 17 |
| Crystal nucleator | Compound 2 | Compound 11 | NA-11 | — |
| Crystallization temperature (° C.) | 136.2 | 131.1 | 130.9 | 131.8 |
| Fluxural modulus (MPa) | 3460 | 3330 | 3340 | 3330 |
| Flexural strength (MPa) | 61.5 | 59.5 | 60.2 | 59.2 |

Example 27

An amount of 100 g of the 4-methylcyclohexane-1,2-dicarboxylic acid calcium salt (compound 3) obtained in Example 3 and 50 g of magnesium laurate (manufactured by Nitto Kasei Kogyo K.K.; hereinafter, abbreviated as "La—Mg") were homogeneously mixed (dry-blended) to prepare a crystal nucleating agent composition.

Three polyolefin resin compositions were prepared as in Example 10 except that the crystal nucleating agent composition obtained above was used instead of the compound 2. The crystallization temperatures and half-crystallization times of the three polyolefin resin compositions obtained were measured. Table 7 shows the results.

Example 28

A crystal nucleating agent composition and three polyolefin resin compositions were prepared as in Example 27 except that zinc laurate (manufactured by Nitto Kasei Kogyo K.K.; hereinafter, abbreviated as "La—Zn") was used instead of La—Mg. The crystallization temperatures and half-crystallization times of the three polyolefin resin compositions obtained were measured. Table 7 shows the results.

Example 29

A crystal nucleating agent composition and three polyolefin resin compositions were prepared as in Example 27 except that aluminum stearate (mono-, di- and tri-mixture; manufactured by Nitto Kasei Kogyo K.K.; hereinafter, abbreviated as "St-Al") was used instead of La—Mg. The crystallization temperatures and half-crystallization times of the three polyolefin resin compositions obtained were measured. Table 7 shows the results.

Example 30

A crystal nucleating agent composition and three polyolefin resin compositions were prepared as in Example 27 except that zinc stearate (manufactured by Nitto Kasei Kogyo K.K.; hereinafter, abbreviated as "St-Zn") was used instead of La—Mg. The crystallization temperatures and half-crystallization times of the three polyolefin resin compositions obtained were measured. Table 7 shows the results.

Example 31

A crystal nucleating agent composition and three polyolefin resin compositions were prepared as in Example 27 except that magnesium 12-hydroxystearate (manufactured by Nitto Kasei Kogyo K.K.; hereinafter, abbreviated as "12HSt-Mg") was used instead of La—Mg. The crystallization temperatures and half-crystallization times of the three polyolefin resin compositions obtained were measured. Table 7 shows the results.

Example 32

A crystal nucleating agent composition and three polyolefin resin compositions were prepared as in Example 27 except that lithium 12-hydroxystearate (manufactured by Nitto Kasei Kogyo K.K.; hereinafter, abbreviated as "12HSt-Li") was used instead of La—Mg. The crystallization temperatures and half-crystallization times of the three polyolefin resin compositions obtained were measured. Table 7 shows the results.

Reference Example 1

A crystal nucleating agent composition and three polyolefin resin compositions were prepared as in Example 30 except that the cyclohexane-1,2-dicarboxylic acid calcium salt (compound 11) obtained in Comparative Example 2 was used instead of the compound 3. The crystallization temperatures and half-crystallization times of the three polyolefin resin compositions obtained were measured. Table 7 shows the results.

Reference Example 2

Three polyolefin resin compositions were prepared as in Example 27 except that La—Mg was not mixed, and the compound 3 was used alone. The crystallization temperatures and half-crystallization times of the three polyolefin resin compositions obtained were measured. Table 7 shows the results.

TABLE 7

| | | Example | | | | | | | Reference Example | |
|---|---|---|---|---|---|---|---|---|---|---|
| | | 27 | 28 | 29 | 30 | 31 | 32 | | 1 | 2 |
| Crystal nucleator | | Compound 3 | Compound 3 | Compound 3 | Compound 3 | Compound 3 | Compound 3 | | Compound 11 | Compound 3 |
| Fatty acid metal salt | Type | La—Mg | La—Zn | St—Al | St—Zn | 12HSt—Mg | 12HSt—Li | | St—Zn | — |
| | Amount (parts by mass) | 50 | 50 | 50 | 50 | 50 | 50 | | 50 | — |
| Crystallization temperature (° C.) | twin | 135.3 | 135.8 | 135.5 | 135.9 | 135.3 | 135.9 | | 132.2 | 135.7 |
| | single50 | 134.6 | 135.4 | 134.8 | 135.6 | 134.8 | 135.0 | | 131.6 | 134.5 |
| | single25 | 134.2 | 135.2 | 134.3 | 135.2 | 134.6 | 134.8 | | 127.7 | 134.3 |
| Half-crystallization time (seconds) | twin | 51 | 46 | 52 | 49 | 48 | 47 | | 72 | 47 |
| | single50 | 54 | 50 | 54 | 51 | 56 | 56 | | 101 | 60 |
| | single25 | 56 | 52 | 58 | 51 | 61 | 61 | | 106 | 62 |

Example 33

An amount of 100 g of the 4-methylcyclohexane-1,2-dicarboxylic acid calcium salt (compound 3) obtained in Example 3 and 50 g of magnesium laurate (manufactured by Nitto Kasei Kogyo K.K.; hereinafter, abbreviated as "La—Mg") were homogeneously mixed (dry-blended) to prepare a crystal nucleating agent composition.

An amount of 100 parts by mass of a polypropylene homopolymer (MFR: 30 g/10 min (load: 2160 g, temperature: 230° C.)) as a polyolefin resin, 0.1 parts by mass of the crystal nucleating agent composition obtained as described above as a crystal nucleating agent, 0.05 parts by mass of calcium stearate (manufactured by Nitto Kasei Kogyo K.K.), and 0.05 parts by mass of tetrakis[methylene-3-(3,5-di-tert-butyl-4-hydroxyphenyl)propionate]methane (trade name "IRGANOX1010" manufactured by BASF Japan Ltd.) and 0.05 parts by mass of tris(2,4-di-tert-butylphenyl) phosphite (trade name "IRGAFOS168" manufactured by BASF Japan Ltd.) as different additives were dry-blended.

Subsequently, three polyolefin resin compositions were prepared as in Example 10 using the dry-blended product obtained above, and the crystallization temperatures and half-crystallization times of the three polyolefin resin compositions obtained were measured. Table 8 shows the results.

Example 34

A crystal nucleating agent composition and three polyolefin resin compositions were prepared as in Example 33 except that lithium laurate (manufactured by Nitto Kasei Kogyo K.K.; hereinafter, abbreviated as "La—Li") was used instead of La—Mg. The crystallization temperatures and half-crystallization times of the three polyolefin resin compositions obtained were measured. Table 8 shows the results.

Example 35

A crystal nucleating agent composition and three polyolefin resin compositions were prepared as in Example 33 except that St-Al was used instead of La—Mg. The crystallization temperatures and half-crystallization times of the three polyolefin resin compositions obtained were measured. Table 8 shows the results.

Example 36

A crystal nucleating agent composition and three polyolefin resin compositions were prepared as in Example 33 except that St-Zn was used instead of La—Mg. The crystallization temperatures and half-crystallization times of the three polyolefin resin compositions obtained were measured. Table 8 shows the results.

Example 37

A crystal nucleating agent composition and three polyolefin resin compositions were prepared as in Example 33 except that 12HSt-Mg was used instead of La—Mg. The crystallization temperatures and half-crystallization times of the three polyolefin resin compositions obtained were measured. Table 8 shows the results.

Example 38

A crystal nucleating agent composition and three polyolefin resin compositions were prepared as in Example 33 except that aluminum 12-hydroxystearate (manufactured by Nitto Kasei Kogyo K.K.; hereinafter, abbreviated as "12HSt-Al") was used instead of La—Mg. The crystallization temperatures and half-crystallization times of the three polyolefin resin compositions obtained were measured. Table 8 shows the results.

Example 39

A crystal nucleating agent composition and three polyolefin resin compositions were prepared as in Example 33 except that 12HSt-Li was used instead of La—Mg. The crystallization temperatures and half-crystallization times of the three polyolefin resin compositions obtained were measured. Table 8 shows the results.

Example 40

A crystal nucleating agent composition and three polyolefin resin compositions were prepared as in Example 33 except that zinc 12-hydroxystearate (manufactured by Nitto Kasei Kogyo K.K.; hereinafter, abbreviated as "12HSt-Zn") was used instead of La—Mg. The crystallization temperatures and half-crystallization times of the three polyolefin resin compositions obtained were measured. Table 8 shows the results.

Reference Example 3

A crystal nucleating agent composition and three polyolefin resin compositions were prepared as in Example 36 except that the cyclohexane-1,2-dicarboxylic acid calcium salt (compound 11) obtained in Comparative Example 2 was used instead of the compound 3. The crystallization temperatures and half-crystallization times of the three polyolefin resin compositions obtained were measured. Table 8 shows the results.

Reference Example 4

Three polyolefin resin compositions were prepared as in Example 33 except that La—Mg was not mixed, and the compound 3 was used alone. The crystallization temperatures and half-crystallization times of the three polyolefin resin compositions obtained were measured. Table 8 shows the results.

TABLE 8

|  |  | Example |  |  |  |  |  |  |  | Reference Example |  |
|---|---|---|---|---|---|---|---|---|---|---|---|
|  |  | 33 | 34 | 35 | 36 | 37 | 38 | 39 | 40 | 3 | 4 |
| Crystal nucleator |  | Compound 3 | Compound 3 | Compound 3 | Compound 3 | Compound 3 | Compound 3 | Compound 3 | Compound 3 | Compound 11 | Compound 3 |
| Fatty acid metal salt | Type | La—Mg | La—Li | St—Al | St—Zn | 12HSt—Mg | 12HSt—Al | 12HSt—Li | 12HSt—Zn | St—Zn | — |
|  | Amount (parts by mass) | 50 | 50 | 50 | 50 | 50 | 50 | 50 | 50 | 50 | — |
| Crystallization temperature (° C.) | twin | 134.0 | 133.9 | 133.7 | 134.3 | 134.7 | 133.8 | 135.0 | 134.7 | 132.0 | 133.9 |
|  | single50 | 133.7 | 133.5 | 132.9 | 134.2 | 134.7 | 133.5 | 134.9 | 134.6 | 131.3 | 133.0 |
|  | single25 | 133.6 | 133.3 | 132.1 | 134.2 | 134.6 | 133.3 | 134.9 | 134.5 | 127.1 | 132.8 |
| Half-crystallization time (seconds) | twin | 53 | 58 | 62 | 58 | 51 | 61 | 51 | 54 | 76 | 69 |
|  | single50 | 69 | 74 | 70 | 59 | 55 | 77 | 56 | 58 | 108 | 83 |
|  | single25 | 72 | 76 | 80 | 59 | 62 | 80 | 61 | 62 | 113 | 87 |

INDUSTRIAL APPLICABILITY

The crystal nucleating agent containing a metal salt of an alicyclic dicarboxylic acid of the present invention, when added to a polyolefin resin, can significantly improve the crystallization rate, i.e. the crystallization temperature, of the polyolefin resin to shorten the molding cycle for a large member or the like by half, for example, considerably contributing to cost reduction, prevention of troubles during processing, and the like. The crystal nucleating agent containing a metal salt of an alicyclic dicarboxylic acid of the present invention can improve the crystallinity to achieve not only improvement of the mechanical performance (e.g., rigidity), optical performance (e.g., transparency), and thermal performance (e.g., heat resistance) of the resulting molded article, but also reduction of shrinkage and warpage, enabling stable production of a molded article even in a complicated shape. Further, even when used in combination with a filler such as talc, the crystal nucleating agent is capable of exhibiting an excellent effect, and can be effectively used even in applications which require rigidity, strength, and the like. The crystal nucleating agent containing a metal salt of an alicyclic dicarboxylic acid of the present invention therefore can be widely used for various applications such as automotive members, electric members, mechanical components, daily goods, cases for clothes, and containers for food by taking advantage of the characteristics described above.

The invention claimed is:

1. A metal salt of an alicyclic dicarboxylic acid,
the alicyclic dicarboxylic acid being an alkyl substituent-containing cyclohexane-1,2-dicarboxylic acid,
the metal salt being a calcium salt, a hydroxyaluminum salt, a disodium salt, or a dilithium salt,
wherein the metal salt comprises 85 mol % or higher of a cis isomer, wherein both oxycarbonyl groups are in a cis orientation to at least one alkyl substituent.

2. The metal salt of the alicyclic dicarboxylic acid according to claim 1, wherein the alkyl substituent is a C1-C4 linear or branched alkyl group.

3. The metal salt of the alicyclic dicarboxylic acid according to claim 2, wherein the alkyl substituent is a methyl group or a tert-butyl group.

4. The metal salt of the alicyclic dicarboxylic acid according to claim 1, wherein the alkyl substituent is at the 3- or 4-position of the cyclohexane ring.

5. The metal salt of the alicyclic dicarboxylic acid according to claim 1, wherein the metal salt is the calcium salt or the disodium salt.

6. A method for producing the metal salt of the alicyclic dicarboxylic acid according to claim 1, the method comprising:

step 1 of reacting a C5-C8 conjugated diene compound with maleic anhydride to prepare an alkyl substituent-containing 4-cyclohexene-1,2-dicarboxylic anhydride;
step 2 of hydrogenating the alkyl substituent-containing 4-cyclohexene-1,2-dicarboxylic anhydride obtained in step 1 to prepare an alkyl substituent-containing cyclohexane-1,2-dicarboxylic anhydride; and
step 3 of reacting the alkyl substituent-containing cyclohexane-1,2-dicarboxylic anhydride obtained in step 2 with a metal oxide, a metal hydroxide, or a metal chloride to prepare the metal salt of the alkyl substituent-containing cyclohexane-1,2-dicarboxylic acid.

7. A crystal nucleating agent for polyolefin resins comprising the metal salt of the alicyclic dicarboxylic acid according to claim 1.

8. A crystal nucleating agent composition for polyolefin resins comprising:
the crystal nucleating agent for the polyolefin resins according to claim 7, and
a metal salt of a C12-C22 saturated or unsaturated fatty acid optionally having at least one hydroxy group in a molecule.

9. The crystal nucleating agent composition for the polyolefin resins according to claim 8, wherein the metal of the metal salt of the C12-C22 saturated or unsaturated fatty acid optionally having the at least one hydroxy group in the molecule is lithium, magnesium, aluminum, or zinc.

10. A polyolefin resin composition comprising:
the crystal nucleating agent for the polyolefin resins according to claim 7, and
a polyolefin resin.

11. The polyolefin resin composition according to claim 10, further comprising a metal salt of a C12-C22 saturated or unsaturated fatty acid optionally having at least one hydroxy group in a molecule.

* * * * *